(12) United States Patent
Tachauer et al.

(10) Patent No.: US 8,608,721 B2
(45) Date of Patent: Dec. 17, 2013

(54) COMPOSITE FASTENER PRODUCTS

(75) Inventors: Ernesto S. Tachauer, Bedford, NH (US); Wallace L. Kurtz, Jr., Lunenburg, MA (US); Brian J. Vanbenschoten, Rochester, NH (US); Joseph E. Pierce, Appleton, WI (US); Arthur E. Garavaglia, Alpharetta, GA (US); Scott M. Filion, Newmarket, NH (US); William P. Clune, Northwood, NH (US); Christopher M. Gallant, Nottingham, NH (US); Nadezhda Efremova, Neenah, WI (US)

(73) Assignee: Velcro Industries B.V., Willemstad, Curacao ( * ) Notice: Subject to any disclaimer, the term of this patent is extended or adjusted under 35 U.S.C. 154(b) by 0 days.

(21) Appl. No.: 13/242,396

(22) Filed: Sep. 23, 2011

(65) Prior Publication Data

US 2012/0009380 A1 Jan. 12, 2012

Related U.S. Application Data

(62) Division of application No. 10/703,696, filed on Nov. 6, 2003, now Pat. No. 8,079,995.

(51) Int. Cl.
*A61F 13/15* (2006.01)

(52) U.S. Cl.
USPC .......... 604/391; 604/387; 604/389; 604/390

(58) Field of Classification Search
USPC .......... 604/389, 391, 387, 390; 156/269, 297, 156/519, 522; 428/100; 24/30.5, 304, 306, 24/450
See application file for complete search history.

(56) References Cited

U.S. PATENT DOCUMENTS

| | | | |
|---|---|---|---|
| 4,761,318 A | 8/1988 | Ott et al. | |
| 5,260,015 A | 11/1993 | Kennedy et al. | |
| 5,582,606 A | 12/1996 | Bruemmer et al. | |
| 6,051,094 A * | 4/2000 | Melbye et al. | 156/269 |
| 6,180,205 B1 | 1/2001 | Tachauer et al. | |
| 6,205,623 B1 | 3/2001 | Shepard et al. | |
| 6,372,954 B1 | 4/2002 | Johnston et al. | |
| 6,419,667 B1 | 7/2002 | Avalon et al. | |
| 6,481,063 B2 | 11/2002 | Shepard | |
| 6,520,946 B1 | 2/2003 | Krueger | |
| 6,531,207 B1 | 3/2003 | Eaton et al. | |
| 6,554,816 B1 | 4/2003 | Olson | |
| 2003/0085485 A1 | 5/2003 | Seidel et al. | |
| 2003/0087059 A1 | 5/2003 | Jackson et al. | |
| 2003/0087098 A1 | 5/2003 | Eaton et al. | |
| 2003/0104746 A1 | 6/2003 | Menzies et al. | |

* cited by examiner

*Primary Examiner* — Jacqueline F. Stephens
(74) *Attorney, Agent, or Firm* — Fish & Richardson P.C.

(57) ABSTRACT

Methods and systems including an engageable material with a lane of plastic resin extending across an interface of first and second ends of an article, wherein the plastic resin is bonded to the first and second ends such that the first and second ends are joined by the resin; and an array of fastener elements extending from one side of the plastic resin. The fastener elements include engageable heads on stems integrally formed with the lane of the plastic resin such that the two ends releasably engage the engageable material to secure the article.

12 Claims, 20 Drawing Sheets

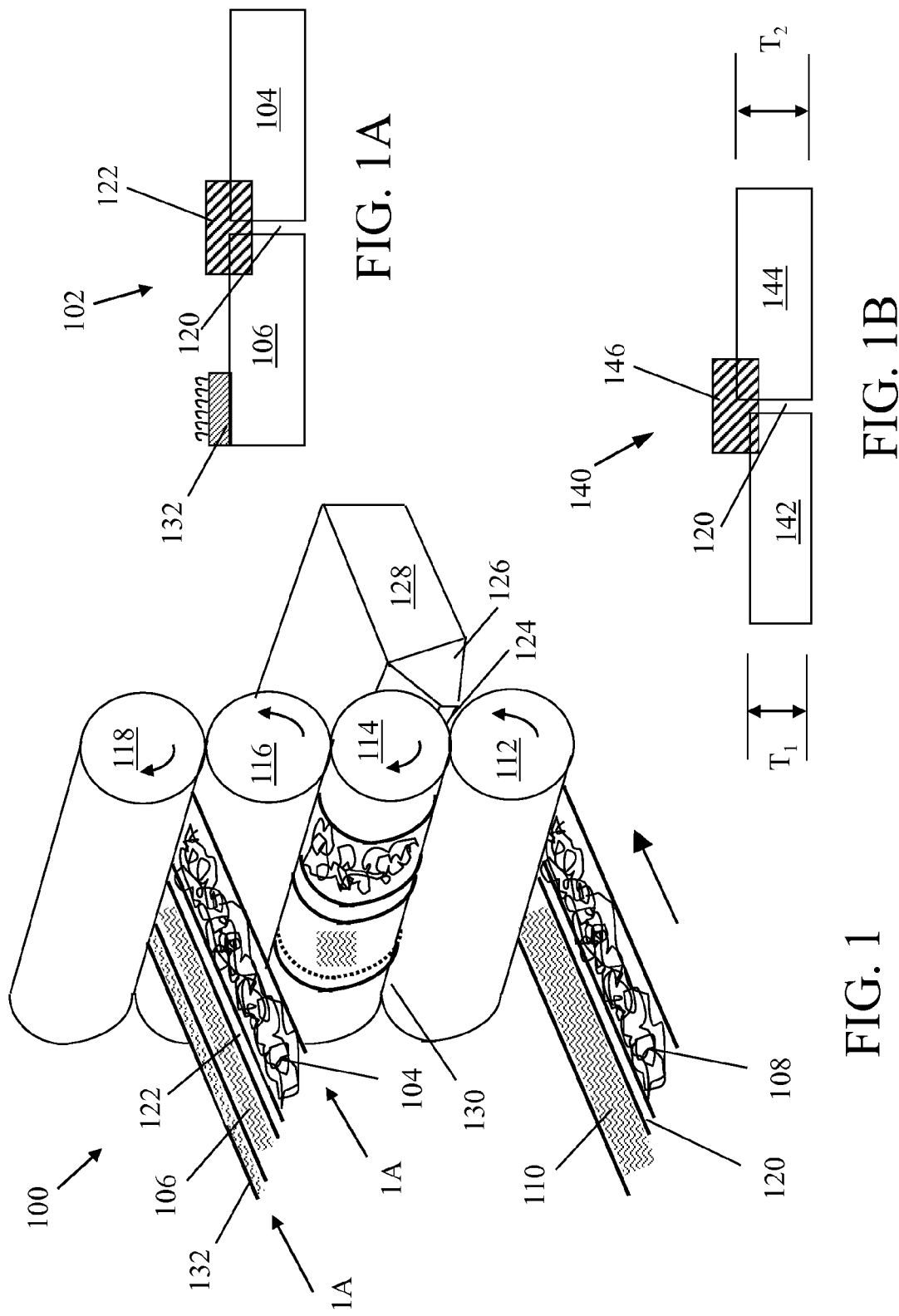

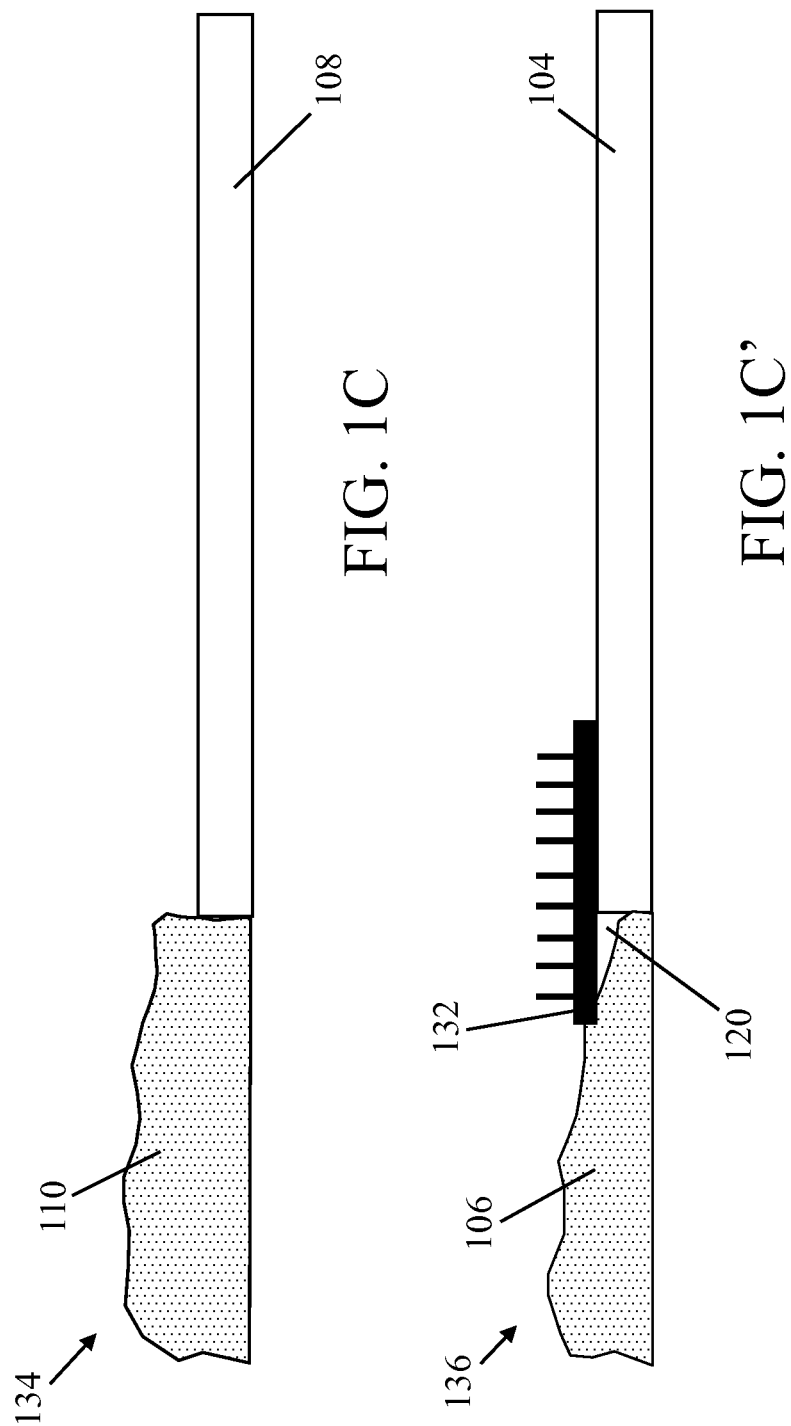

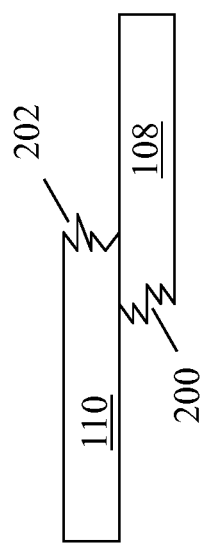
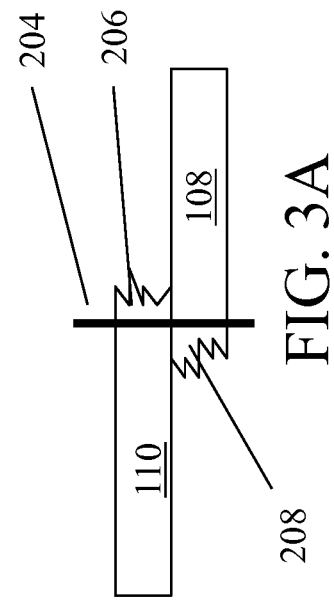

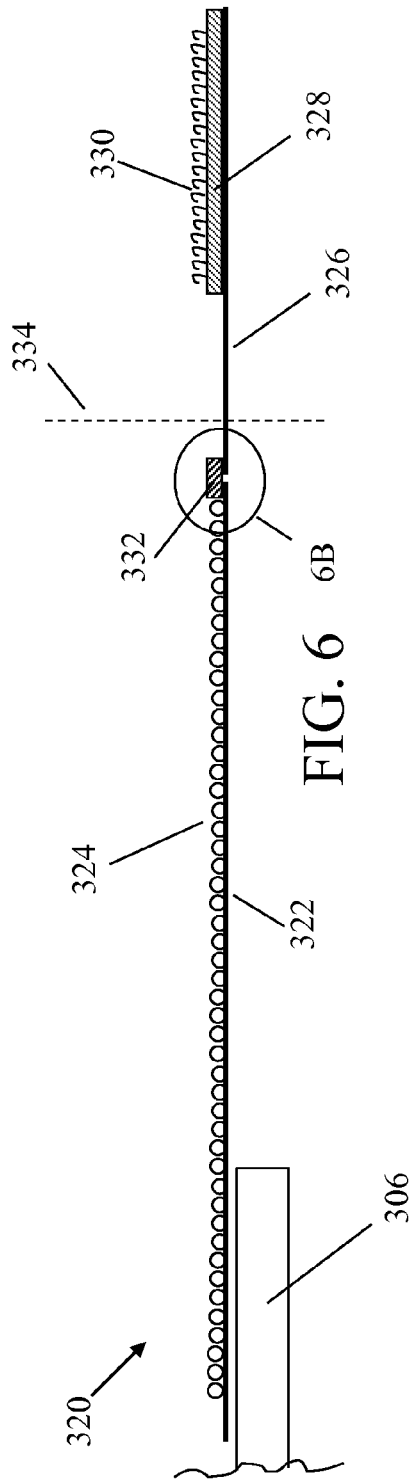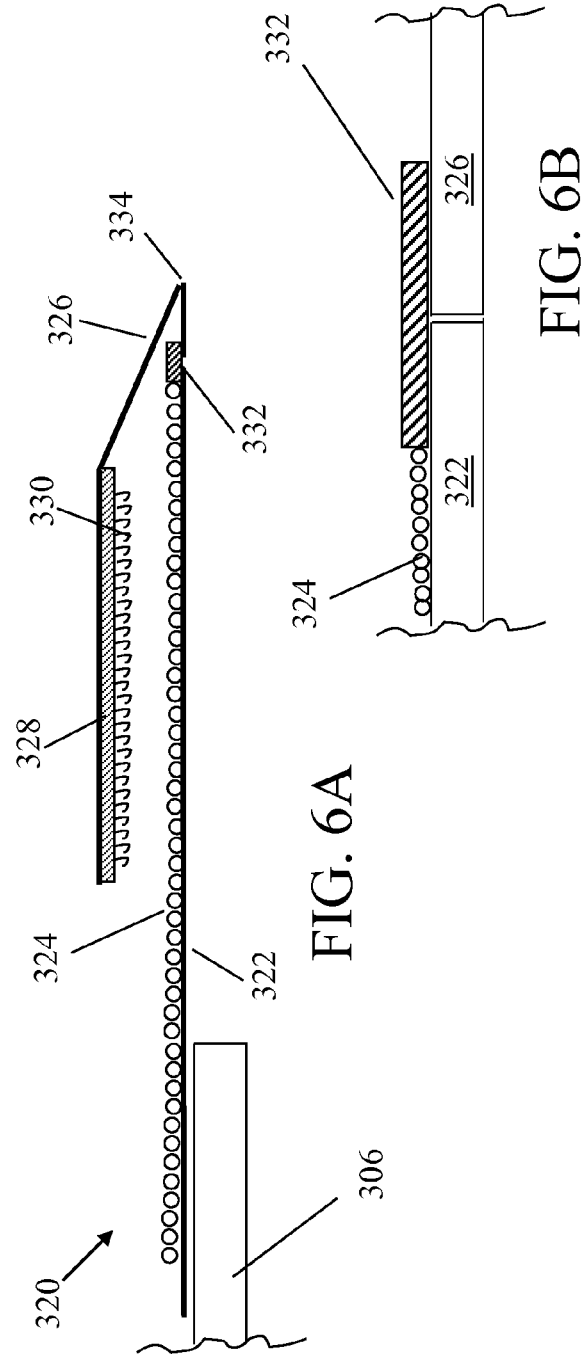

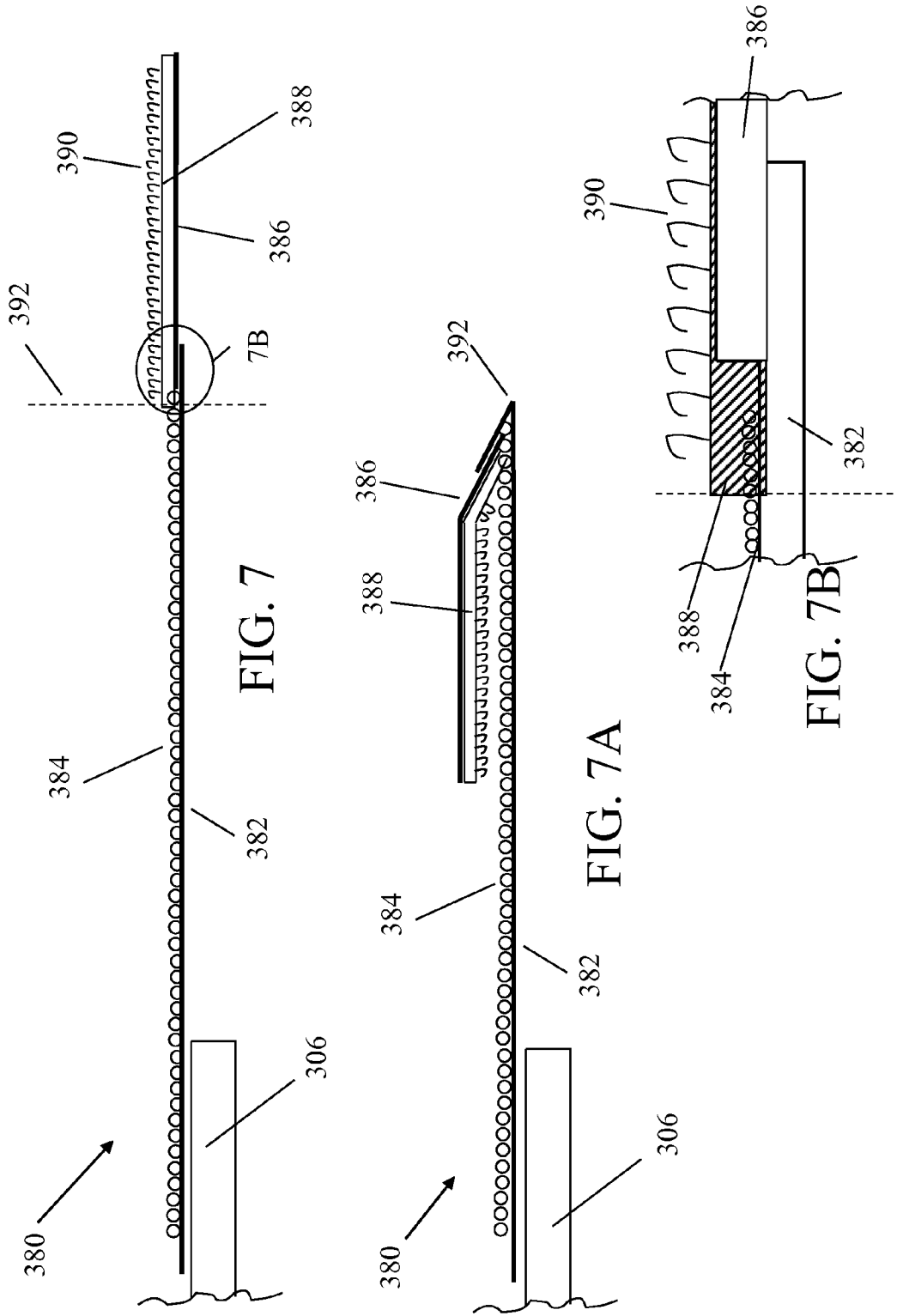

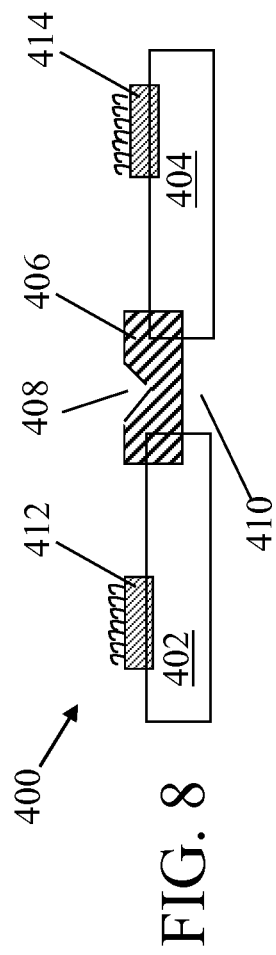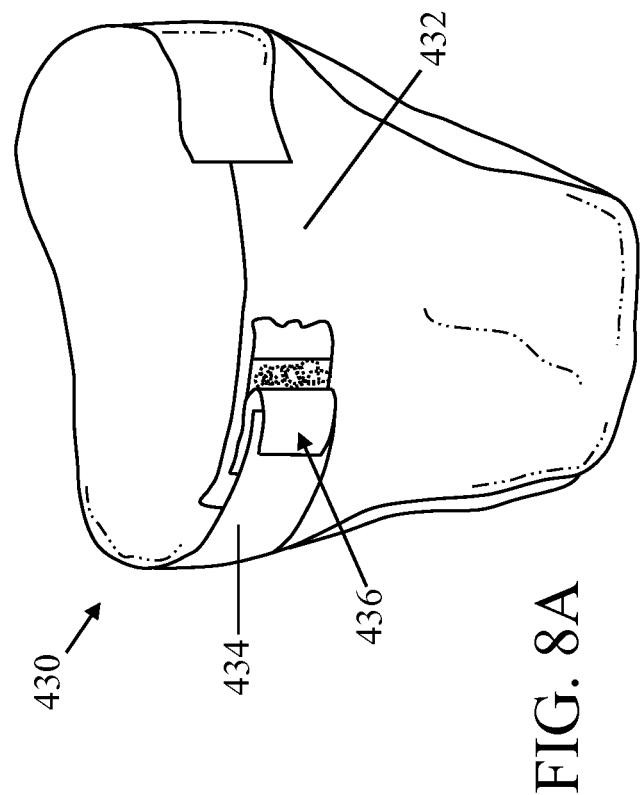

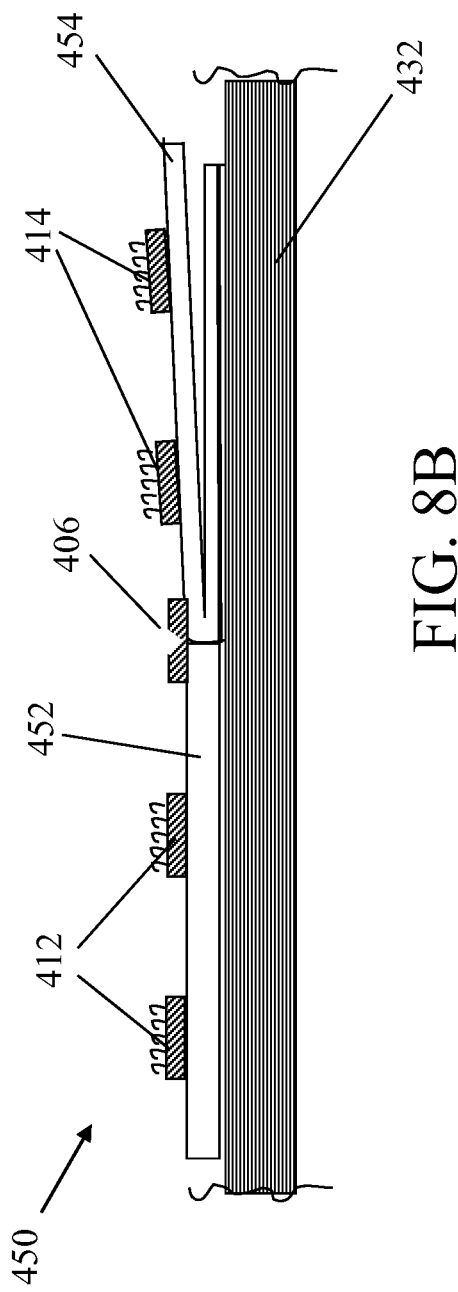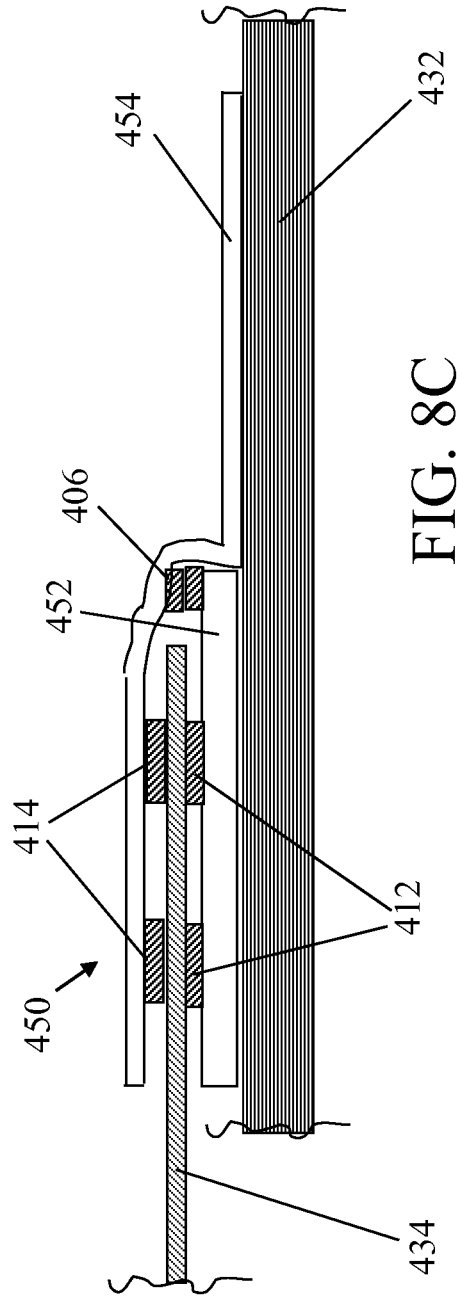

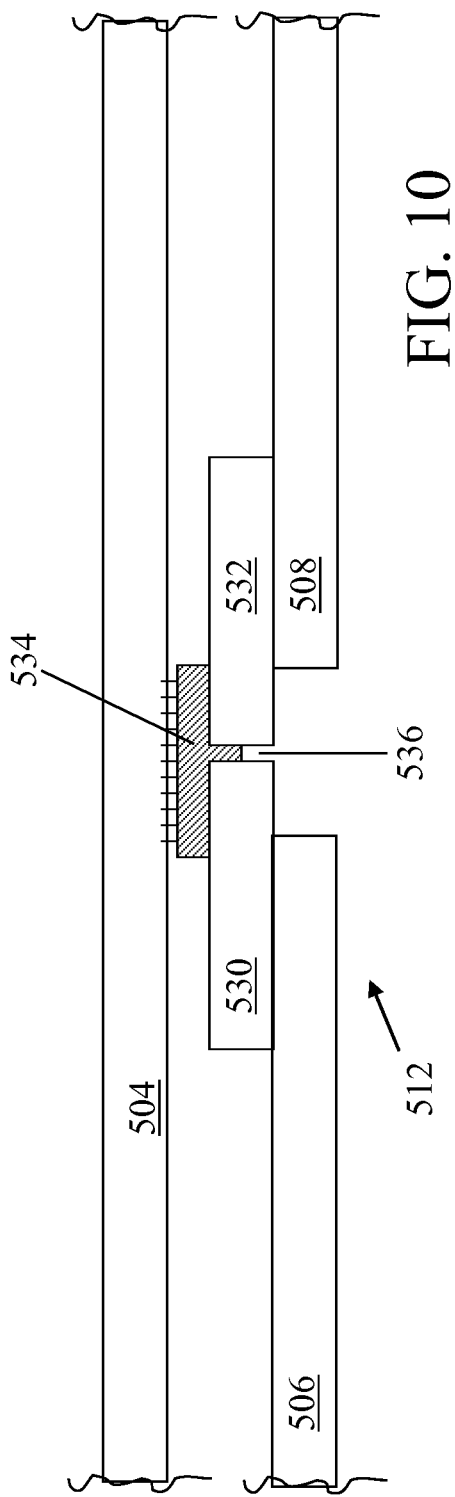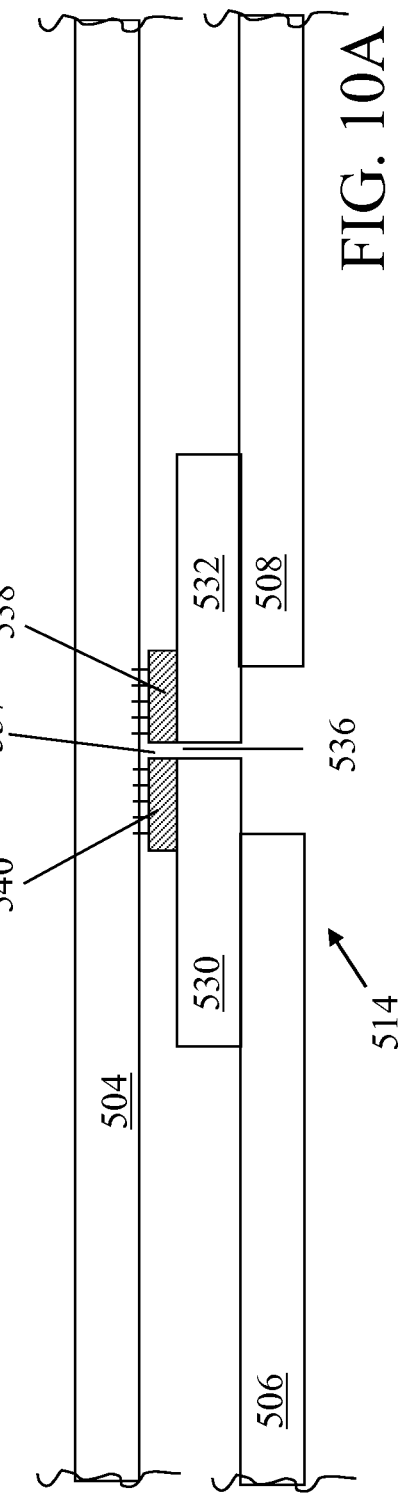

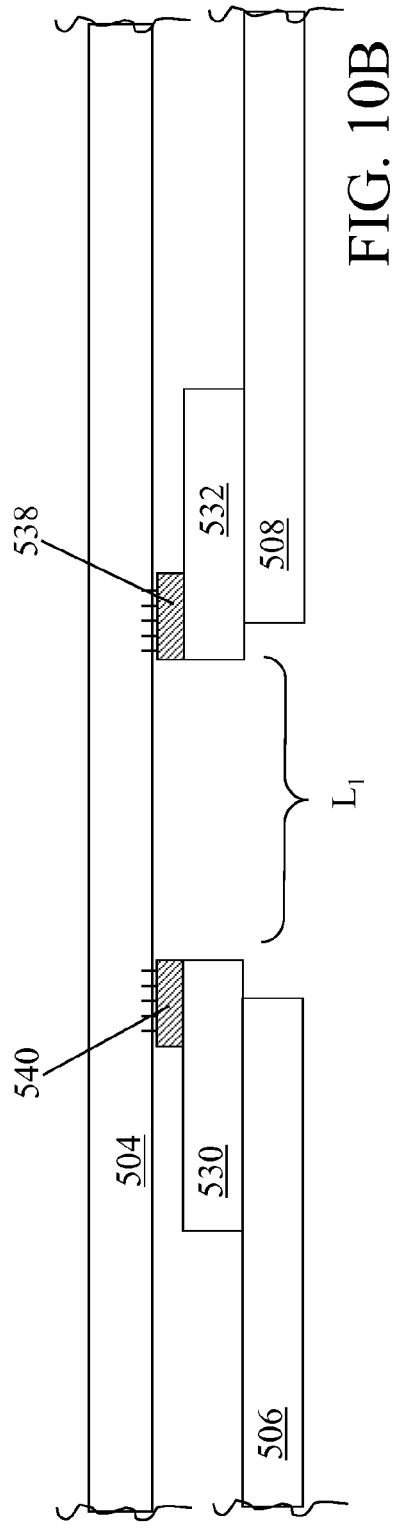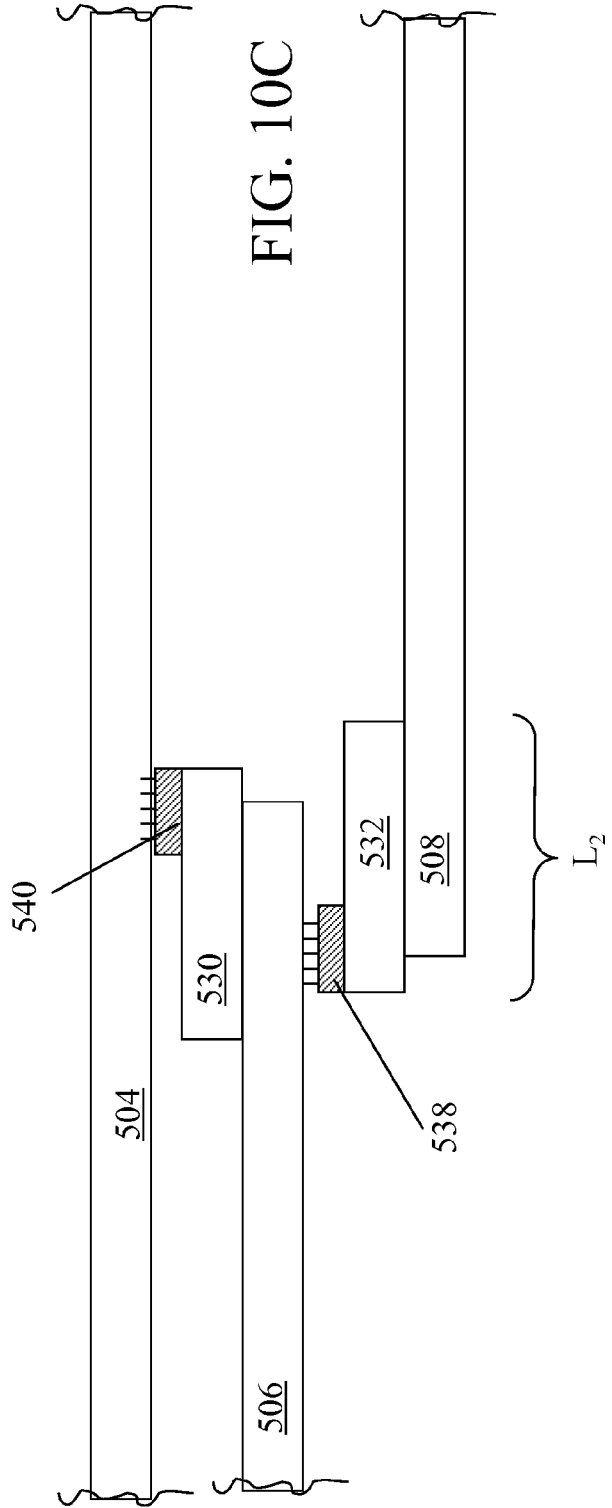

COMPOSITE FASTENER PRODUCTS

CROSS-REFERENCE TO RELATED APPLICATIONS

This application is a divisional (and claims the benefit of priority under 35 U.S.C. 121) of U.S. application Ser. No. 10/703,696, filed Nov. 6, 2003 now U.S. Pat. No. 8,079,995. The disclosure of the prior applications is considered part of (and is incorporated by reference in its entirety in) the disclosure of this application.

TECHNICAL FIELD

This invention relates to composite fastener products, such as those having both male and female touch fastener elements, and to sheet material laminates.

BACKGROUND

Composite hook and loop or other engageable fastener products are known to be produced by taking preformed hook and loop or other engageable material and overlapping and attaching the two materials together, such as along their edge margins, by ultrasonic welding, thermal fusing or adhesive bonding, for example.

Some hook fastener tape is produced in a continuous molding process, in which a plastic resin strip base is molded with integral fastener element stems extending from one surface. Typically, this molding is performed in a high pressure nip, such as between two counter-rotating rollers or against a single roller that defines miniature cavities in its peripheral surface, for molding either fastener element stems or complete fastener elements. To fill the miniature cavities at a high rate of speed, significant nip pressure is required. The nip is typically quite thin, for molding a correspondingly thin and flexible fastener element base. Because of the delicate nature of the surface of the molding roll, and the expense of producing such rolls, care must be taken to avoid roll surface damage.

Kennedy et al., U.S. Pat. No. 5,260,015, disclosed that, with proper controls, some preform sheet materials could be introduced to the nip for in situ lamination to the base of the fastener element tape while the tape was being molded, under conditions that would not impede the filling, cooling and removal of fastener element stems from their respective cavities, nor cause local damage to the molding roll surface. More recently, Shepard et al., U.S. Pat. No. 6,205,623, have disclosed introducing two or more identical sheets to the nip in parallel, with gaps between them, and forming fastener tapes across the gaps.

Further improvements in the formation of fastener composite materials, and in the materials themselves, are desired.

SUMMARY

In one aspect, the invention features a method of manufacturing a composite fastener material. The method includes providing two longitudinally continuous sheets of material, positioning the two sheets to form a longitudinal, continuous interface between the two sheets, joining the two sheets by introducing one or more molten plastic resins in at least one lane, one lane of the resin extending across the interface under conditions that cause the resin to bond to the two sheets, molding an array of stems from at least one lane of the resin, the stems extending from an exposed surface of the composite material, and forming engageable heads on the stems to form fastener elements, wherein the two sheets differ from one another by one of material composition, thickness, texture, stretchability, breathability, and compressability.

In some embodiments of the invention the two sheets are permanently joined. In some other cases, the two sheets are joined in such a manner as to enable later separation.

In some configurations, a second array of stems is molded from the at least one lane of the resin, the stems extending from a second exposed surface of the composite material.

The two sheets differ from one another by material composition in some examples. For instance, in one case one of the two sheets is a neck bonded laminate, and the other of the sheets is a point unbonded non-woven material.

In some instances, the two sheets differ from one another by thickness. Preferably, one of the sheets has a nominal thickness that differs from a nominal thickness of the other sheet by more than about 0.0001 inch. For some applications, it is preferred that one of the sheets has a nominal thickness that differs from a nominal thickness of the other sheet by less than about 0.2 inch.

For some uses, the two sheets differ from one another by texture. For example, one of the sheets has a generally smooth surface to which the resin bonds, and the other of the sheets has interstices into which the resin flows. In another example, one of the sheets is a fabric, and the other of the sheets is a polymer film. The fabric may be knit fabric, woven, needle punched non-woven, spunbond, point unbonded non-woven material (PUB), neck bonded laminate (NBL), spunbond-meltblown-spunbond multi-layer laminate (SMS), stretched bonded laminate (SBL), meltblown non-woven, air laid non-woven, and air formed non-woven.

NBL is a composite elastic necked-bonded material including at least one necked material joined to at least one elastic sheet. By 'necked-bonded laminate' we mean a laminate material formed by bonding a necked material to an elastic sheet material, where the term "necked material" refers to any material which has been narrowed in at least one dimension by application of a tensioning force.

PUB is a fabric pattern having continuous thermally bonded areas defining a plurality of discrete unbonded areas.

Spunbond refers to a nonwoven web of spunbond fibers that is produced by melt spinning. The spunbond fibers are small diameter fibers which are formed by extruding molten thermoplastic material as filaments from a plurality of fine, usually circular capillaries of a spinneret, with the diameter of the extruded filaments then being rapidly reduced. Spunbond non-woven material can be formed from polyester, nylon, or polyolefins.

SMS is a laminate with three layers: spunbond, meltblown, and spunbond. Such a laminate may be made by sequentially depositing onto a moving forming belt first a spunbond fabric layer, then a meltblown fabric layer and last another spunbond layer and then bonding the laminate such as by thermal point bonding.

SBL can be formed by tensioning an elastomeric sheet material and bonding a gatherable web (e.g., a spunbond polypropylene web) to the tensioned sheet material by application of pressure, the bonding being accomplished due to the adhesivity of the elastomeric sheet material and without application of heat for softening the sheet material and/or gatherable web.

The film may be polyethylene in any of its versions, polypropylene, poly vinyl chloride, polyamide, polyester, thermoplastic olefin, and thermoplastic elastomer. In another case, one of the sheets is paper, and the other of the sheets is a polymer film. The paper may be polymer coated or tissue paper.

In some embodiments, the lane of the resin extending across the interface is a lane of the resin from which the array of stems are molded. In some embodiments, joining the two sheets includes continuously feeding the two sheets through a nip defined between a rotating mold roll and a pressure roll, the rotating mold roll defining an array of cavities about its periphery for molding the array of stems, while continuously introducing the molten plastic resin to the mold roll under conditions which cause the resin to fill the cavities of the mold roll and form the lane of resin extending across the interface, pressure in the nip bonding the two sheets to the lane of resin extending across the interface. In some embodiments, the loop engageable heads are integrally formed with the stems. In some embodiments, forming the loop-engageable heads on the stems is performed after the array of stems is molded.

At least one of the two sheets may be non-woven loop material. In one case, at least one of the two sheets is spunbond. In another case, one of the two sheets is point unbonded non-woven material. In another case, one of the sheets is neck bonded laminate. In another case, one of the two sheets is spunbond-meltblown-spunbond multi-layer laminate.

In some embodiments, at least one of the two sheets includes plastic film. In some embodiments, the one plastic lane is formed from polyethylene in any of its versions, polypropylene, poly vinyl chloride, polyamide, polyester, thermoplastic olefin, and thermoplastic elastomer.

In some embodiments, positioning the two sheets includes positioning the two sheets in contact at the interface. In a preferred embodiment, positioning the two sheets in contact at the interface includes overlapping the two sheets to create an overlap section between the two sheets, cutting along a line in the overlap section, and discarding the free strips. In this preferred embodiment, the line is curved. In this preferred embodiment, joining the two sheets may include forming a curved plastic lane using a moveable resin head moving along a curvature of the curved line.

In some embodiments, the one lane of the resin extending across the interface is wider than the interface. In some examples, the method includes introducing molten plastic resin in at least two additional lanes, one on each of the two sheets, molding an array of stems from the additional lanes, the stems extending from an exposed surface of the composite material, and forming loop-engageable heads on the stems on at least one of the additional lanes to form fastener elements. In other examples, the method includes forming a folding feature in the one lane of resin extending across the interface in which case the method may further include folding one of the two sheets such that a fold line is at the interface or placing a first sheet from the two sheets on a second sheet from the two sheets.

In some embodiments, the method includes providing a third longitudinally continuous sheet of material, positioning the third sheet to form a second longitudinal, continuous gaps or overlaps between the third sheet and one of the two sheets, joining the three sheets by introducing molten plastic resin in a second lane, the second lane of the resin extending across the gaps or overlaps under conditions that cause the resin to bond to the third sheet and one of the two sheets, molding a second array of stems from the second lane of the resin, the stems extending from an exposed surface of the composite material, and forming engageable heads on the stems to form fastener elements. In one example, the method also includes forming a splitting feature in the second lane of resin.

In another aspect, the invention features a composite fastener material. This composite fastener material includes a length of a first material, a length of a second material, at least one longitudinal lane of plastic resin extending across a longitudinal, continuous interface of the two materials, wherein the plastic resin is bonded to the first and second materials such that the first and second materials are joined by the resin, and an array of fastener elements extending from one side of the composite fastener material, the fastener elements comprising engageable heads on stems integrally formed with one lane of the plastic resin, wherein the second material differs from the first material by one of material composition, thickness, texture, stretchability, breathability, and compressability.

In some embodiments, the one longitudinal lane of plastic resin is continuous. In some examples, the first and second materials differ from one another by material composition; for instance one of the two materials is neck bonded laminate and the other of the materials is spunbond. In other examples, the first and second materials differ from one another by color, texture, or breathability; for instance one of the two materials is a first type of spunbond, and the other of the materials is a second type of spunbond. In other examples, the two materials differ from one another by thickness; for instance one of the materials has a nominal thickness that differs from a nominal thickness of the other materials by more than about 0.0001 inch or one of the materials has a nominal thickness that differs from a nominal thickness of the other material by less than about 0.2 inch.

In other examples, the two materials differ from one another by texture; for instance one of the materials has a generally smooth surface to which the resin bonds, and the other of the materials defines interstices into which the resin flows. In some of these examples, one of the materials includes foam. In some of these examples, one of the materials is a fabric, and the other of the materials is a polymer film. In these examples, the fabric may be knit fabric, woven, needle punched non-woven, spunbond, point unbonded non-woven material, neck bonded laminate, spunbond-meltblown-spunbond multi-layer laminate, meltblown non-woven, air laid non-woven, and air formed non-woven. In these examples, the film may be polyethylene in any of its versions, polypropylene, poly vinyl chloride, polyamide, polyester, thermoplastic olefin, and thermoplastic elastomer. In some of these examples, one of the materials is paper, and the other of the materials is a polymer film. In these examples, the paper is polymer coated or tissue paper.

In some embodiments, the stems are integrally formed with the lane of plastic resin extending across the interface of the two materials. In some other embodiments, composite fastener material includes a fastening tab with an end configured to be permanently attached to a diaper chassis. In some of these other embodiments with this fastening tab, the lane of the plastic resin with which the fastener elements are integrally formed is preferably located on the second material and is spaced apart from the longitudinal lane of plastic resin extending across the longitudinal, continuous interface of the two materials. In some of these other embodiments with this fastening tab, the longitudinal lane of plastic resin is continuous. In some of these other embodiments with this fastening tab, the lane of the plastic resin with which the fastener elements are integrally formed is the one longitudinal lane of plastic resin extending across the longitudinal, continuous interface of the two materials.

In some embodiments, the composite fastener material includes a length of a third material and at least one longitudinal lane of plastic resin extending across a longitudinal, continuous interface of the third material with a second material from the two materials, wherein the plastic resin is bonded to the third material and the second material such that the third and second materials are permanently joined by the resin. In some cases, the longitudinal lane of plastic resin has an array of fastener elements extending from one side, the fastener elements comprising engageable heads on stems integrally formed with the lane of plastic resin. In some of these cases, the longitudinal lane of plastic resin is continuous.

In some embodiments, the longitudinal lane of plastic resin extending across the longitudinal, continuous interface of the two materials has a folding feature and the lane is spaced apart from the one lane of the plastic resin with which the fastener elements are integrally formed. In some cases, the composite fastener material includes, on the first material, a second lane of the plastic resin with which the fastener elements are integrally formed and the second material is unfolded about the fold line to releasably engage the two sides of the loop material on the one end of the diaper chassis. In some cases, the composite fastener material includes, on the first material, a second lane of the plastic resin with which the fastener elements are integrally formed and the second material is overlayed on top of the first material.

For some embodiments the folding feature is a V-shaped notch.

In another aspect, the invention features a first disposable absorbent article. This first disposable absorbent article includes a chassis having opposite ends, an engageable material attached to the chassis adjacent to one of the ends, and a fastening tab extending from the chassis adjacent to another of the ends, and arranged to releasably engage the engageable material to secure the disposable absorbent article to a wearer, wherein the fastening tab comprises the composite fastener material described above.

In some embodiments, the engageable material has hook engageable loops.

In some embodiments, a peel force of the engaged fastening tab with the chassis is stronger than the force to separate the bond of the plastic resin from the first material and the second material.

In some embodiments, the one lane of the plastic resin with which the fastener elements are integrally formed is located on the second material and is spaced apart from the one longitudinal lane of plastic resin extending across the longitudinal, continuous interface of the two materials. In some cases, the composite fastener material includes a third material, wherein the one lane of the plastic resin with which the fastener elements are integrally formed extends across the longitudinal, continuous interface of the second material and the third material and the one lane is bonded to the second material and the third material such that the second material and the third material are permanently joined by the resin, a fourth material, at least one longitudinal lane of plastic resin extending across a longitudinal, continuous interface of the third material with the fourth material, wherein the plastic resin is bonded to the third material and the fourth material such that the third and fourth materials are permanently joined by the resin, and an array of fastener elements extending from one side of the composite fastener material, the fastener elements comprising engageable heads on stems integrally formed with one lane of the plastic resin.

In some embodiments, the one lane of the plastic resin with which the fastener elements are integrally formed includes the one longitudinal lane of plastic resin extending across the longitudinal, continuous interface of the two materials.

In another aspect, the invention features a second disposable absorbent article. The second disposable absorbent article includes a chassis having opposite ends and a double closure system attached to the chassis adjacent to one of the ends, wherein the double closure system is arranged to releasably engage two sides of the one end to secure the diaper to a wearer. In this case, the double closure system can include the composite fastener material described above wherein the composite fastener material further includes a fold line at the folding feature. Furthermore, in some examples, the composite fastener material also includes, on the first material, a second lane of the plastic resin with which the fastener elements are integrally formed and the second material is unfolded about the fold line to releasably engage the two sides of the engageable material on the one end of the diaper chassis. In this case, for some examples, the composite fastener material further includes, on the first material, a second lane of the plastic resin with which the fastener elements are integrally formed and the second material is unfolded from being overlayed on top of the first material about the fold line to releasably engage the two sides of the engageable material on the one end of the chassis.

In another aspect, the invention features a third disposable absorbent article. The third disposable absorbent article includes a chassis having a first end and a second end that are opposite to one another, an engageable material attached to the chassis adjacent to the two ends, a lane of plastic resin extending across an interface of the first and second ends, wherein the plastic resin is bonded to the first and second ends such that the first and second ends are joined by the resin, and an array of fastener elements extending from one side of the plastic resin, the fastener elements including engageable heads on stems integrally formed with the lane of the plastic resin such that the two ends releasably engage the engageable material to secure the disposable absorbent article to a wearer.

In some embodiments, the engageable material has hook engageable loops. In some embodiments, the first and second ends form a butt joint. In some embodiments, the lane of plastic resin is splittable to enable disengaging the first end from the second end and thereby removing the disposable absorbent article from the wearer. In some embodiments, the lane of plastic resin is splittable to form a first lane of plastic resin with engageable heads on the first end, and a second lane of plastic resin with engageable heads on the second end. In some cases, the lane of plastic resin is splittable to enable reattaching the two ends to the engageable material of the chassis to change a fit and a size of the disposable absorbent article.

In another aspect, the invention features a second method for joining two substrates of different materials with plastic strips using fastening techniques such as ultrasonic welding or applying adhesive. In some examples, the plastic strips have hook or hook-like fasteners. This second method includes forming a hook strip and then ultrasonically welding (or some other form of adhering) the hook strip to two substrates of different materials. Alternatively, the second method includes ultrasonically welding (or some other form of adhering) a pre-formed hook strip to two substrates of different materials.

These and other embodiments may have one or more of the following advantages. By using a calender stack to continuously mold two or more preformed materials together into multiple substrates and simultaneously mold hook fasteners on areas of the preformed materials, new and useful composite materials can be economically manufactured. This continuous manufacturing method eliminates discrete steps in the manufacturing process to assemble the multiple substrates. After manufacture, these composite materials can be subsequently cut into separate strips for application in diapers, absorbent articles, and other personal and non-personal care articles. The combination of the multiple substrates in the composite strips enable special functionality in application. Substrates of incompatible material compositions can be joined by a molded strip of resin carrying useful fastener elements.

The details of one or more embodiments of the invention are set forth in the accompanying drawings and the description below.

DESCRIPTION OF DRAWINGS

FIG. 1 is a diagrammatic perspective view, of a calender-forming-and-uniting machine producing a continuous composite web material.

FIG. 1A is a cross section view of the composite web material of FIG. 1.

FIG. 1B is a cross section view of a different composite material formed using the apparatus of FIG. 1.

FIG. 1C is a view of two different materials before being joined using the apparatus of FIG. 1.

FIG. 1C' is a view of the different materials of FIG. 1C after being joined into a composite material using the apparatus of FIG. 1.

FIG. 3 is a view of two overlapped substrates with uneven edges.

FIG. 3A is a view of a cut line through the two substrates of FIG. 3.

FIG. 6 is a side view of a diaper tab formed from a composite web material.

FIG. 6A is a side view of the diaper tab of FIG. 6 folded for storage.

FIG. 6B is a magnified side view of the permanent joining of two substrates to form the composite web material of FIG. 6.

FIG. 7 is a side view of a diaper tab formed from a composite web material.

FIG. 7A is a side view of the diaper tab of FIG. 7 folded for storage.

FIG. 7B is a magnified side view of the permanent joining of two substrates to form the composite web material of FIG. 7.

FIG. 8 is a schematic side view of a composite web material with two substrates and a notched plastic strip permanently joining the two substrates.

FIG. 8A is a view of a diaper with a diaper flap releasably attached to a diaper chassis using a double closure fastener.

FIG. 8B is a view of a double closure fastener of FIG. 8A in an open position.

FIG. 8C is a view of a double closure fastener of FIG. 8A in a closed position releasably attached to a diaper flap.

FIG. 10 is a view of the tear fastener of FIG. 9.

FIG. 10A is a view of the tear fastener of FIG. 10 in a torn state.

FIG. 10B is a view of the absorbant articles of FIG. 9A reattached to increase the size of the opening.

FIG. 10C is a view of the tear fastener of the absorbant articles of FIG. 9B reattached to decrease the size of the opening.

Like reference symbols in the various drawings indicate like elements.

DETAILED DESCRIPTION

Figure 1E:
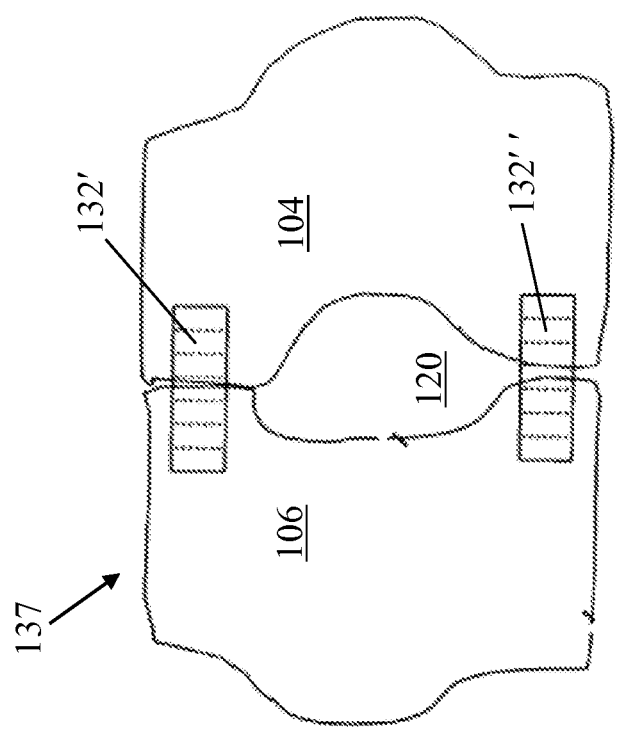
FIG. 1E is a view of the composite material of FIG. 1D in a stretched state.

Referring to FIGS. 1 and 1A, calender stack 100 manufactures a continuous, composite material such as material 102 for multiple applications requiring composite materials formed from heterogeneous materials and touch fasteners. The method builds upon the continuous extrusion/roll-forming method for molding fastener elements on an integral, sheet-form base described by Fischer in U.S. Pat. No. 4,794,028, and the nip lamination process described by Kennedy, et al. in U.S. Pat. No. 5,260,015, the details of both of which are incorporated herein by reference. Material 102 includes two substrates 104 and 106 that are preformed materials 108, 110, respectively, that differ by material composition, thickness, texture, stretchability, breathability, or compressability. Materials 108 and 110 can be formed from knit fabric, woven, non-woven loop material such as neck bonded laminate (NBL), point unbonded non-woven material (PUB), spunbond non-woven material (hereafter referred to as spunbond), spunbond-meltblown-spunbond multi-layer laminate (SMS), stretched bonded laminate (SBL), and meltblown non-woven, air laid non-woven, and air formed non-woven.

NBL is a composite elastic necked-bonded material including at least one necked material joined to at least one elastic sheet. By 'necked-bonded laminate' we mean a laminate material formed by bonding a necked material to an elastic sheet material, where the term "necked material" refers to any material which has been narrowed in at least one dimension by application of a tensioning force. Examples of NBL materials are described in U.S. Pat. No. 5,226,992 by Mormon, the entire disclosure of which is hereby incorporated by reference in a manner that is consistent herewith.

PUB is a fabric pattern having continuous thermally bonded areas defining a plurality of discrete unbonded areas. PUB is described in U.S. Pat. No. 5,964,742 by McCormack et al., the entire disclosure of which is hereby incorporated by reference in a manner that is consistent herewith.

Spunbond refers to a nonwoven web of spunbond fibers that is produced by melt spinning. The spunbond fibers are small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 by Appel et al., the entire disclosure of which is hereby incorporated by reference in a manner that is consistent herewith. Spunbond non-woven material can be formed from polyester, nylon, or polyolefins.

SMS is a laminate with three layers: spunbond, meltblown, and spunbond. Such a laminate may be made by sequentially depositing onto a moving forming belt first a spunbond fabric layer, then a meltblown fabric layer and last another spunbond layer and then bonding the laminate such as by thermal point bonding. SMS materials are well known as shown in U.S. Pat. No. 4,041,203 by Brock et al., the entire disclosure of which is hereby incorporated by reference in a manner that is consistent herewith SBL can be formed by tensioning an elastomeric sheet material and bonding a gatherable web (e.g., a spunbond polypropylene web) to the tensioned sheet material by application of pressure, the bonding being accomplished due to the adhesivity of the elastomeric sheet material and without application of heat for softening the sheet material and/or gatherable web. SBL is described in U.S. Pat. No. 4,789,699 by Kieffer et al., the entire disclosure of which is hereby incorporated by reference in a manner that is consistent herewith.

Materials 108 and 110 can also be formed from plastic polymer film or paper such as polymer coated paper. This enables, for example, combinations of fabrics listed above, foam, and polymer film. This also enables combinations of paper and polymer film. In some cases, different types of spunbond materials can also be combined. The preformed material 108, for instance a material with hook-engageable loops, is introduced as a continuous running length into calender stack 100 comprised of forming rolls 112 and 114 in addition to guide rolls 116 and 118. The preformed material 108 is introduced as a continuous running length into calender stack 100 in parallel with preformed material 110. A continuous interface 120 separates the running lengths of materials 108 and 110. In other examples, interface 120 simply defines a common boundary between materials 108 and 110 such as when materials 108 and 110 are overlapped. The width of interface 120 ranges from approximately zero width (forming a butt joint between materials 108 and 110) to a width limited by the strength of a plastic resin and other factors, after cooling, to join materials 108 and 110 across the width. The calender stack 100 is constructed and arranged to produce a length-wise continuous flat, thin plastic lane 122 by calender action upon a relatively thick sheet of hot, deformable resin 124. Resin 124 can be polyethylene in any of its versions, polypropylene, poly vinyl chloride (PVC), polyamide, polyester, thermoplastic olefin or thermoplastic elastomer. Plastic lane 122 permanently joins materials 108 and 110. The resin 124 is furnished through flat die 126 of extruder 128. The materials 108 and 110 are applied as continuous machine-direction bands upon the plastic lane 122 being continuously formed by the resin material 124 being introduced into the nip 130 of the calender stack 100. Under pressure produced by calender rolls 112 and 114, materials 108 and 110 become embedded or in situ laminated to the plastic resin lane 122 being formed. This causes materials 108 and 110 to be permanently joined together as substrates 104 and 106 of composite material 102 as shown in FIG. 1A.

Due to the pressure produced by calender rolls 112 and 114, the resin material 124 extruded into the gap can flow to bridge the interface between materials 108 and 110 even if materials 108 and 110 differ by thickness or texture. Referring to FIG. 1B, composite material 140 is manufactured using the calender stack of FIG. 1 where material 108 is thinner than material 110. Composite material 140 includes thin substrate 142 and thick substrate 144. Plastic lane 146 joins substrates 142 and 144 such that the portion of plastic lane 146 overlapping substrate 142 is less embedded in substrate 142 than the portion of plastic lane 146 overlapping substrate 144. Materials 108 and 110 can differ in thickness by as much as 0.2 inch or more and as little as 0.0001 inch or less. In this example, material 108 has a nominal thickness $T_1$ of 0.0005 inch and material 110 has a nominal thickness $T_2$ of 0.025 inch. This results in the composite material 140 with substrate 142 having a minimum thickness $T_1$ of 0.0005 inch and substrate 144 having a maximum thickness $T_2$ of 0.025 inch. Materials 108 and 110 can also differ in texture. Plastic resin 124 flows into gaps in the texture of each material, or bonds directly to a smooth surface of the material, thus permanently bonding to the sheet materials. Materials 108 and 110 can include knit loops, woven loops, non-woven loops, smooth plastics, and embossed materials, as examples.

In some examples, substrate 106 is formed from material 110 that is more compressible than material 108 that forms substrate 104. In these examples, the process of FIG. 1 distorts compressible material 110. As shown in FIG. 1C, view 134 shows materials 110 and 108 with interface 120 in a non-stressed state before they are permanently joined together by hook strip 132 using the process of FIG. 1. As shown in FIG. 1C', composite material 136 is the resulting material with substrates 106 and 104 after joining the compressible material 110 with material 108. In composite material 136, substrate 106 is permanently compressed by hook strip 132.

In some examples, the upper roll 114 of the calender stack 100 has mold cavities in its surface that define engageable hooks, stems or other hook preforms, self-engaging formations, or other fastener features. This process, with fixed mold cavities, can produce engageable hooks or hook preforms of a selected desired shape or shapes suitable for post-forming action, etc. Such hooks are designed to be engageable with other hooks or with loops. Extruder 128 provides to the nip 130 additional resin in the form of a molten resin strip of width corresponding to the width of the desired band of molded hooks 132. Completion of the in situ lamination is achieved by the pressure of the calender nip 130 formed by pressure roll 112 and mold roll 114. Resin of this resin strip applied above the material 106 by extruder 128 enters mold cavities in mold roll 114, forming hook band 132 comprising hooks or hook preforms molded integrally with a base resin layer that is in-situ laminated to the material 110 by the action of the calendar nip 130. In other examples, one or more hook bands can also be formed on material 108 in a similar way. Similarly, additional hook bands can be formed on material 110 in a similar way. In some cases, hook band 132 is a continuous band formed according to the techniques disclosed by Kennedy, et al. in U.S. Pat. No. 5,260,015.

Figure 1D:
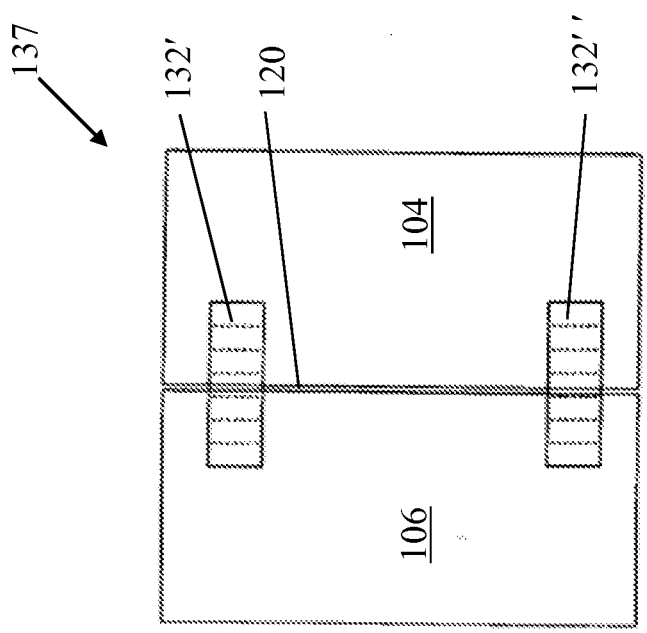
FIG. 1D is a view of a different composite material formed using the apparatus of FIG. 1.

In some other cases, hook band 132 is formed as a series of discontinuous patches aligned in a row and formed according to techniques disclosed by Provost et al. in PCT patent application US02/16898 (Forming Discrete Fastener Element Regions) and hereby incorporated by reference. As shown in FIG. 1D, a composite material 137 is formed using these techniques with discontinuous hook patches 132' and 132". When substrates 104 and 106 in composite material 137 are formed from stretchy materials 108 and 110, and composite material 137 is stretched, gaps due to puckering in a vertical direction can appear in interface 120 between substrates 104 and 106. As shown in FIG. 1E, composite material 137 is stretched with a gap due to puckering in interface 120. Thus, these discontinuous hook patches 132' and 132" enable composite material 137 to be stretched. This is useful for applications where composite material 137 is required to stretch without tearing substrates 106, 104 or plastic lane 132 permanently joining substrates 106, 104.

After plastic lane 122 and hook band 132 are formed in mold roll 114 and laminated to form the composite material 102, guide rolls 116 and 118 guide the continuous composite material 102 away from mold roll 114 and roll the material 102 up in a supply roll (not shown). The finished continuous composite material 102 can be cut at a selected repeat length, either to complete a product, or to complete a subassembly of a product. In other examples, composite material 102 can be formed from three or more preformed materials with no or one or more hook bands by feeding the preformed materials into calender stack 100 in a similar fashion to the example of FIG. 1.

Figure 1F:
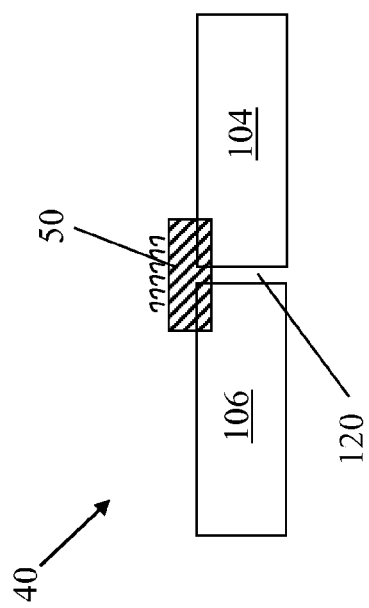
FIGS. 1F and 1G are cross section views of composite web materials formed using the apparatus of FIG. 1.

In an alternate embodiment 40, shown in FIG. 1F, substrates 104 and 106 are joined by hook strip 50 using a modification of the calender stack 100 of FIG. 1. In this modification, calender stack 100 is configured with mold cavities to form the hook strip 50 over the interface 120 to join substrates 104 and 106. Hook strip 50 can have an array of engageable hooks, stems or other hook preforms, self-engaging formations, or other fastener features.

Figure 1G:
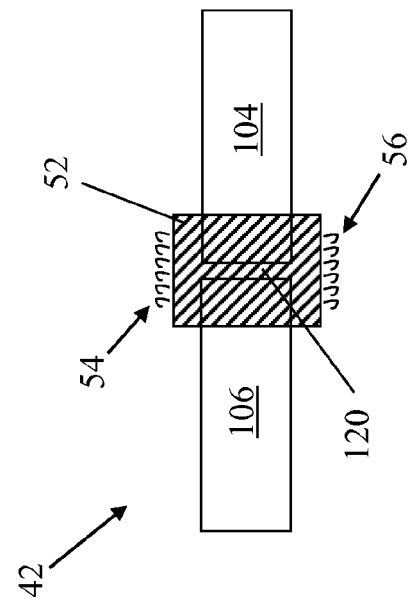

In an alternate embodiment 42, shown in FIG. 1G, substrates 104 and 106 are joined by hook strip 52 using another modification of the calender stack 100 of FIG. 1. In this modification, calender stack 100 is configured with mold cavities to form the hook strip 52 over the gap 120 to join substrates 104 and 106. Hook strip 52 has an array of engageable hooks, stems or other hook preforms, self-engaging formations, or other fastener features on both sides 54, 56 of the interface 120. Embodiment 42 is manufactured by modifying the calender stack 100 such that forming roll 112 also has mold cavities and two additional extruders are provided to apply resin to fill the mold cavities of the respective rolls 112 and 114.

Figure 2:
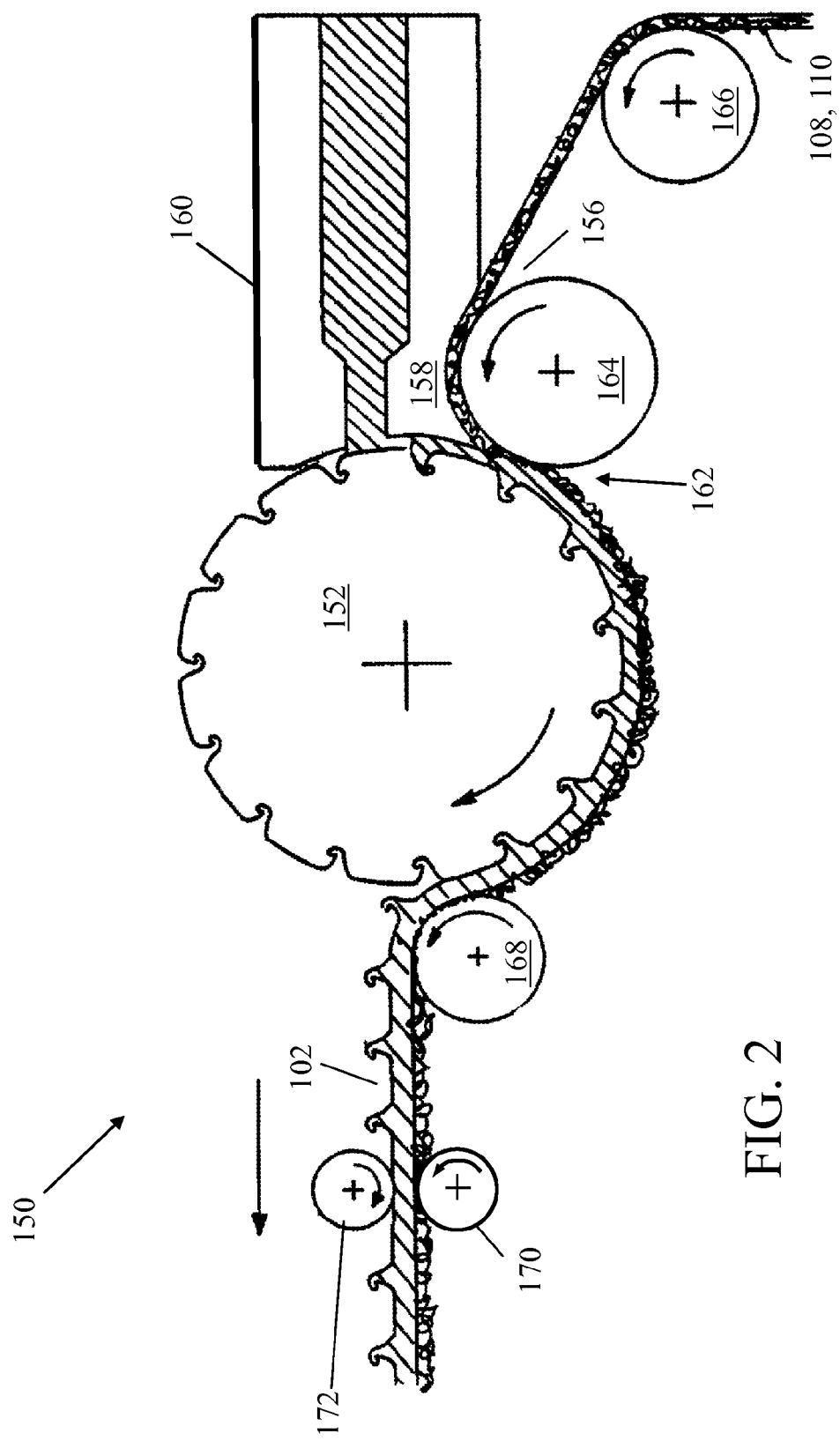
FIG. 2 is a diagrammatic cross-sectional view (thicknesses grossly exaggerated) of another machine forming a material similar to that produced by the machine of FIG. 1.

Referring to FIG. 2, an apparatus 150 can also be employed to form the composite material 102 of FIG. 1A or similar composite materials formed from heterogeneous materials and touch fasteners. The plastic lane 122 that permanently joins materials 108 and 110 and the hook band 132 are formed by mold roll 152 having hook cavities as the plastic from an extruder passes through a gap 156 formed between the mold roll 152 and a complementary-shaped extension 158 of the extrusion die 160. While the resin is still molten, the materials 104 and 106 are introduced side by side and laminated in situ to the resin at a nip 162 formed between the mold roll 152 and pressure application roll 164. At this point the hooks are still in their mold cavities, protected from the effects of laminating pressure. The composite material 102 that includes plastic lane 122 permanently joining materials 104 and 110 along with hook band 132 can thus be produced.

Figure 3B:
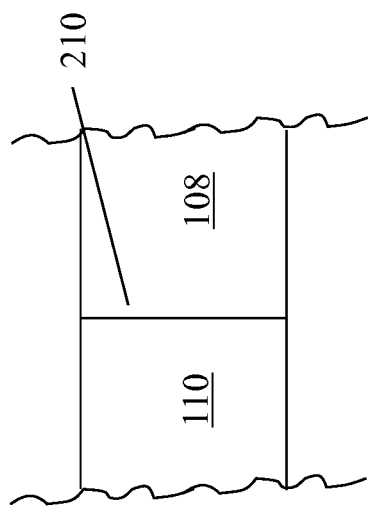
FIG. 3B is a top view of FIG. 3A with a straight cut line.
Figure 3D:
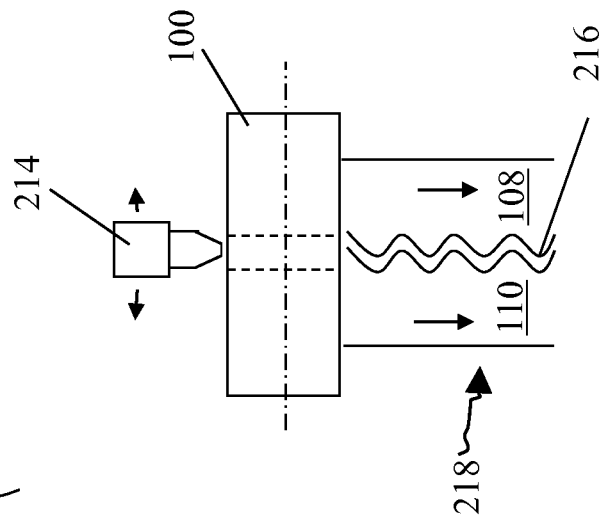
FIG. 3D is a view of a manufacturing process to permanently join the two substrates of FIG. 3C with a curved plastic resin lane using a movable resin extruder.
Figure 3C:
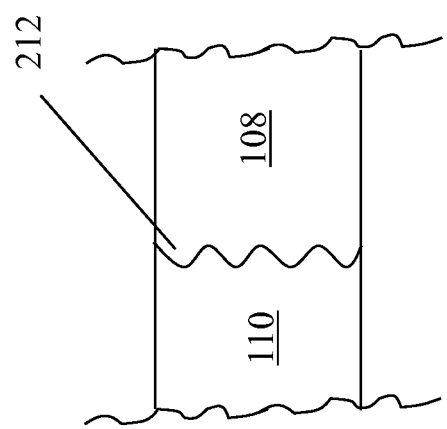
FIG. 3C is a top view of FIG. 3A with a curved cut line.

In some examples, referring to FIG. 3, it is desirable to make interface 120 approximately zero width but uneven surfaces 200, 202 of materials 108 and 110, respectively, make it difficult to feed materials 108 and 110 into calender stack 100 with no separation. Referring to FIG. 3A, materials 108 and 110 are overlaid side by side prior to entering calender stack 100 and continuously cut along cut line 204. Strips 206 and 208 are discarded leaving a clean interface of approximately zero width between materials 108 and 110. In some examples, referring to FIG. 3B, cut line 210 is straight along the continuous running length of materials 108 and 110. In other examples, referring to FIG. 3C, cut line 212 is curved along the continuous running length of materials 108 and 110 and interface 120 is curved. In these examples, referring to FIG. 3D, resin extruder 214 can replace extruder 128 of calender stack 100. Resin extruder 214 is mounted on a motion control system with a degree of freedom such that curved plastic lane 216 is formed on top of curved interface 120 to produce finished composite material 218 with curved plastic lane 216 joining materials 108 and 110.

Figure 4B:
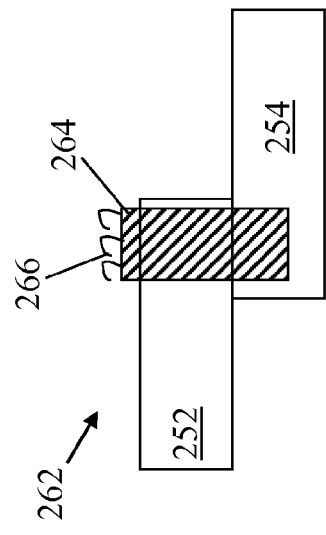
FIGS. 4B and 4C are views of variations of the composite web material of FIG. 1.
Figure 4C:
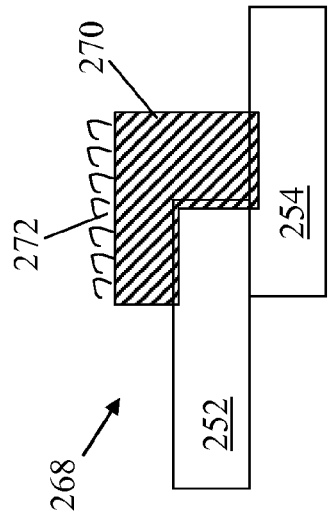
Figure 4:
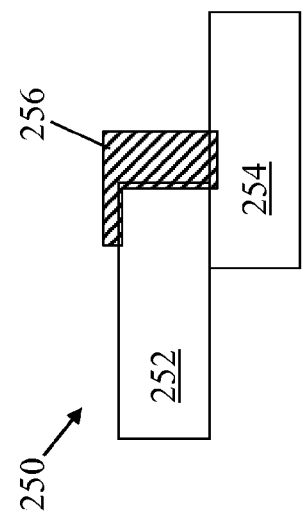
FIGS. 4 and 4A are views of variations of the composite web material of FIG. 1.
Figure 4A:
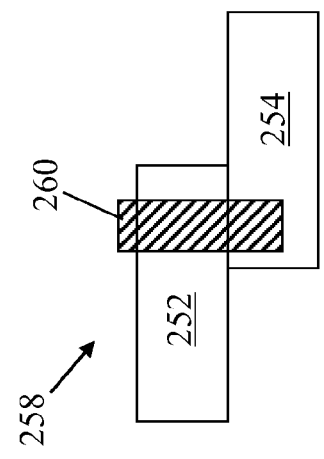

Referring to FIG. 4, a material 250 that is a variation of the above described material can be manufactured using a similar calender stack. Material 250 uses preformed materials 252 and 254 that differ by material composition, thickness, texture, stretchability, breathability, or compressability. Material 250 is formed by feeding material 252 slightly over material 254 such that material 252 overlaps 254. Plastic lane 256 permanently joins materials 252 and 254. Plastic lane 256 is formed in a similar way as plastic lane 122 except that the interface between materials 252 and 254 is an overlap and plastic lane 256 covers the exterior portion of the overlap. In a variation of material 250, referring to FIG. 4A, a material 258 can also be manufactured using calender stack 100 wherein plastic lane 260 penetrates through the overlap between materials 252 and 254. In another variation, referring to FIG. 4B, a material 262 can also be manufactured using a calender stack where plastic lane 264 also penetrates through the overlap between material 252 and 254. However, in this example, the calender stack is configured with a band of mold cavities such that calender stack 100 forms plastic lane 264 with loop-engageable hooks 266 or hook preforms molded integrally with a base resin layer that is in-situ laminated to the materials 252 and 254 by the action of the calendar nip. In still another variation, referring to FIG. 4C, the width of the resin extruded and the band of mold cavities of the calender stack is extended such that plastic lane 272 is formed over the exterior of the overlap of materials 252 and 254 with loop-engageable hooks 272 or hook preforms.

Figure 5:
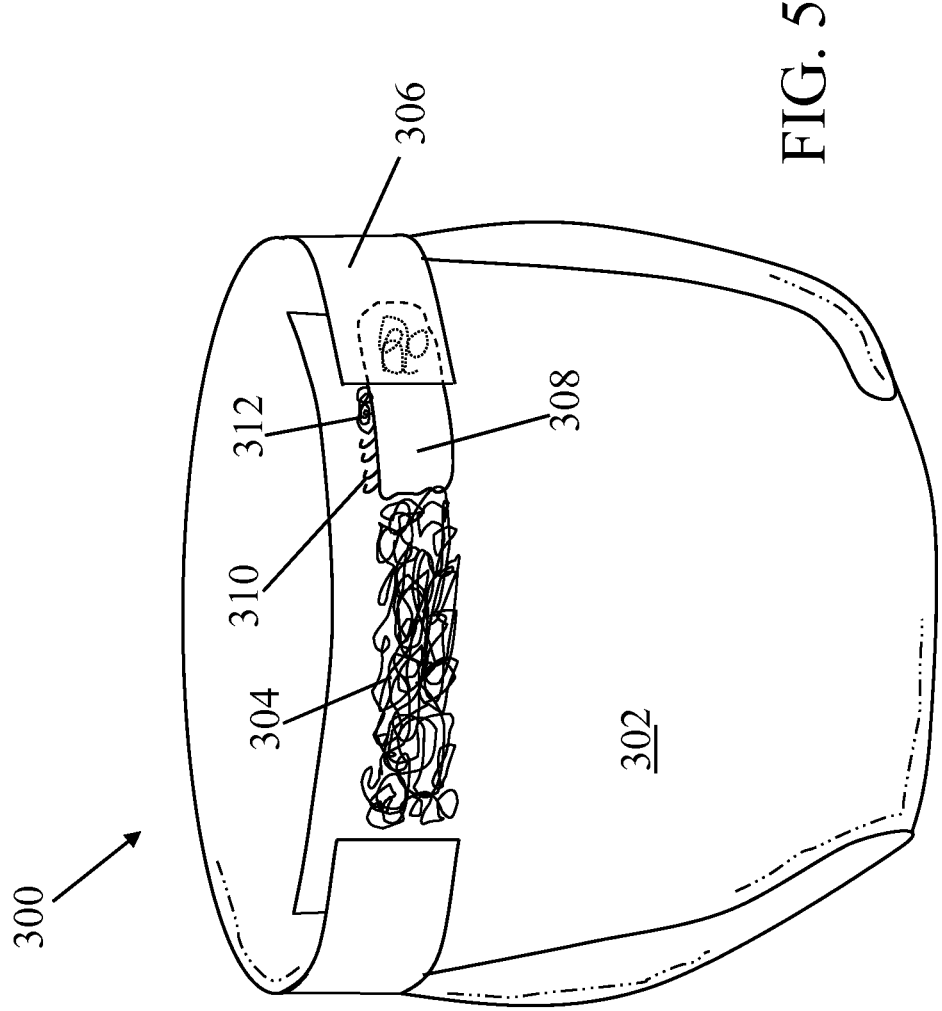
FIG. 5 is a view of a diaper.

Referring to FIG. 5, a diaper 300 includes a chassis 302 with hook-engageable loops 304. Diaper 300 also includes two opposite ends, one of which includes a diaper flap 306. Diaper flap 306 is permanently joined to a diaper tab 308 with hooks 310 for releasably attaching to loops 304 to secure the diaper 300 to a wearer. Diaper tab 308 has loops 312 on the inside such that diaper tab 308 can be folded inwards and hooks 310 of diaper tab 308 can releasably attach to loops 312 for storage. Diaper tab 308 is manufactured by forming a continuous material using the calender stack 100, illustrated in FIG. 1, and then cutting the continuous material at a selected repeat length to form individual diaper tabs 308. Other types of disposable absorbent articles can also be made using individual diaper tabs 308.

Referring to FIG. 6, one example of diaper tab 308 is diaper tab 320. Diaper tab 320 includes stretchy non-woven material 322 with loops 324. In one variation of this example, the non-woven material 322 is NBL. In this variation, diaper tab 320 also includes spunbond material 326 with plastic resin layer 328 having molded hooks 330. Material 322 is permanently joined to spunbond 326 using plastic lane 332. Material 322 is ultrasonically bonded to diaper flap 306. Diaper tab 320 has a fold line 334 such that, as illustrated in FIG. 6A, diaper tab 320 can be folded onto itself and hooks 330 releasably engage with loops 324. A continuous material for creating diaper tab 320 is manufactured using a calender stack by feeding stretchy non-woven material 322 side by side with spunbond 326. The extruder extrudes plastic resin into gap 130 (FIG. 1) creating plastic lane 332, and mold cavities in forming mold 114 (FIG. 1) create plastic lane 328 with hooks 330 or hook preforms. The stretchy quality of non-woven material 322 allows a wearer to stretch diaper tab 320 to form a good fit by releasably engaging hooks 330 with the diaper chassis 302.

Figure 6C:
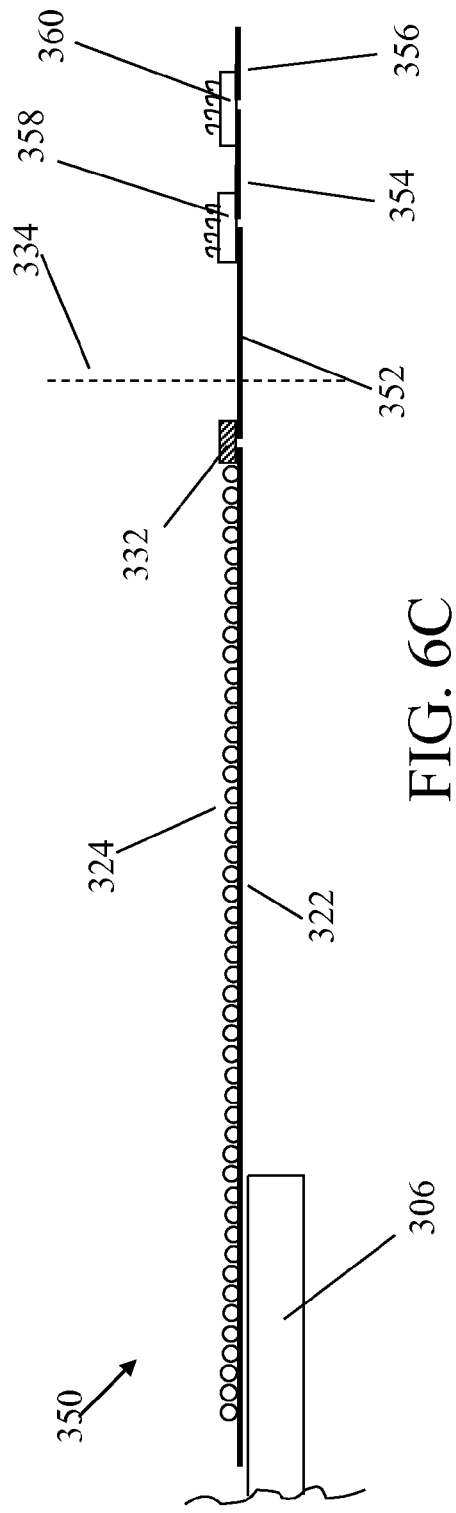
FIG. 6C is a side view of a diaper tab formed from another composite web material.
Figure 6D:
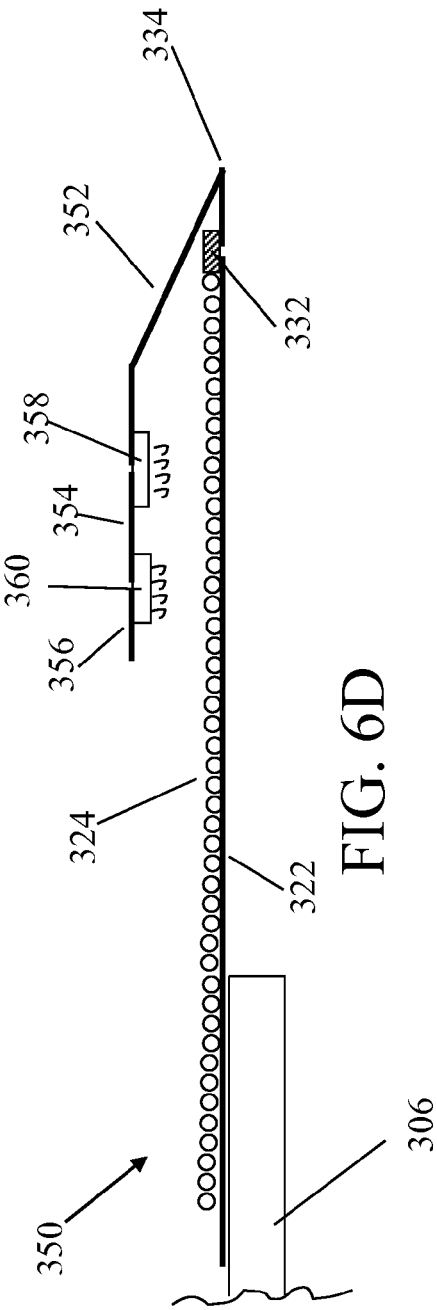
FIG. 6D is a side view of the diaper tab of FIG. 6C folded for storage.

In a variation of the diaper tab 320 of FIG. 6, referring to FIG. 6C, diaper tab 350 includes material 352 joined with non-woven loop material 322 using plastic lane 332. Material 352 is joined to material 354 using plastic lane 358. Material 354 is joined to material 356 using plastic lane 360. Plastic lanes 358 and 360 have hooks molded by bands of hook cavities in a configuration of mold roll 114 (FIG. 1). Diaper tab 350 has fold line 334 such that, as illustrated in FIG. 6D, diaper tab 350 can be folded onto itself and hook lanes 358 and 360 releasably engage with loops 324. The stretchy quality of non-woven material 322 allows a wearer to stretch diaper tab 350 to form a good fit by releasably engaging hook lanes 358 and 360 with the diaper chassis. In some cases, plastic lanes 358 and 360 do not have hooks. In some other cases, plastic lanes 358 and 360 can be formed with a splitting feature such as a perforation.

In a variation of the diaper tab 350 of FIGS. 6C and 6D, the hooks 330 on hook lanes 358 and 360 can be designed so that the mechanical engagement with the hook-engageable loops 304 on diaper chassis 302 is stronger than the lamination of the hook lanes 358 and 360 to materials 352, 354, and 356. In this variation, when the hooks 330 on the hook lanes 358 and 360 are peeled off the loops 304 to unfasten the diaper tab 350 from the diaper chassis 302, the hook lanes 358 and 360 become disengaged from the materials 352, 354, and 356. This variation provides a single use diaper such that a user knows when the diaper has been used before.

The force required to peel off the hook lanes 358 and 360 from the loops 304 can be quantified in terms of pounds per inch of width (PIW). Both the hook lanes 358, 360 and the materials 352, 354, and 356 are subject to the same peel force. For example, the hooks 330 and loops 304 closure can be 5 PIWs. The peeling force required to delaminate the hook lanes 358, 360 from the materials 352, 354, and 356 is "P" and is described as a force per inch of closure width.

If P is greater than about 5 pounds per inch of width, for example, the hook lanes 358, 360 can be peeled off from the hook-engageable loops 304 on diaper chassis 302 with no harm to the lamination of the hook lanes 358 and 360 to materials 352, 354, and 356.

In this same example, if P is less than about 5 pounds per inch of width, however, the hook lanes 358, 360 and loops 304 stay engaged and the hook lanes 358, 360 will delaminate from materials 352, 354, and 356.

Figure 6E:
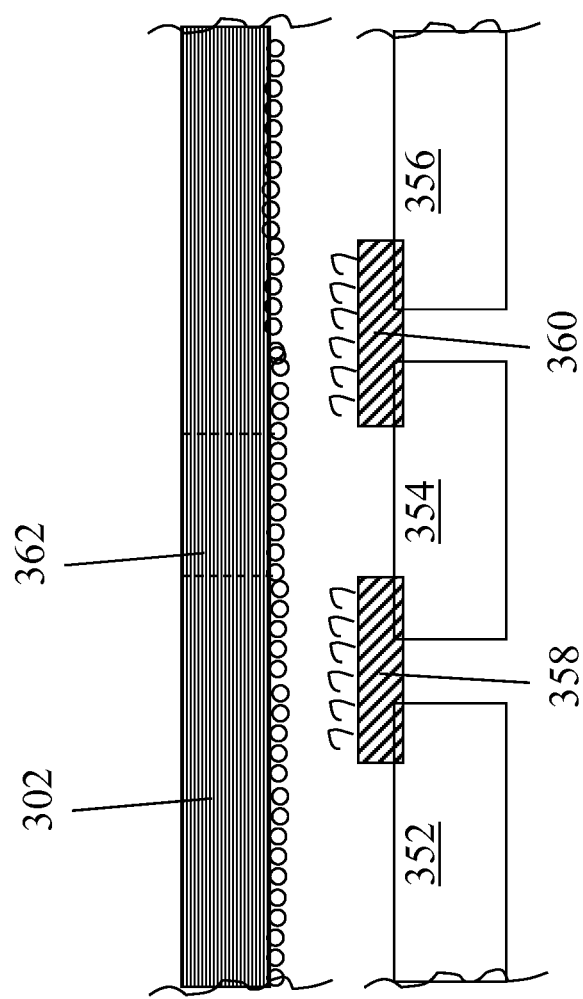
FIG. 6E is a magnified side view of the hook strips portion of the composite material of FIG. 6C releasably attached to loops on a surface of a diaper chassis.

In another variation of the diaper tab 350, during usage after fastening, the diaper can undergo some stretching. Referring to FIG. 6E, loops of diaper chassis 302 releasably attach to hooks in plastic lanes 358 and 360. In some cases, area 362 of diaper chassis 302 stretches as a result of tension from normal usage by a wearer. To prevent unintentional disengagement of the hooks in plastic lanes 358 and 360 from loops of diaper chassis 302, material 354 between plastic hook lanes 358 and 360 can be selected to be stretchy.

Referring to FIG. 7, another diaper tab 380 includes stretchy non-woven material 382 with loops 384. In one variation of this example, non-woven material 382 is NBL. In this variation, diaper tab 380 also includes spunbond material 386. Material 382 is permanently joined to spunbond material 386 using plastic resin layer 388 having molded hooks 390. Material 382 is ultrasonically bonded to diaper flap 306. Diaper tab 320 has a fold line 392 such that, as illustrated in FIG. 7A, diaper tab 380 can be folded onto itself and hooks 390 releasably engage with loops 384. A continuous material for creating diaper tab 380 is manufactured using the calender stack 100 of FIG. 1 by feeding stretchy non-woven material 382 overlaid on spunbond 386. The extruder extrudes plastic resin into the gap creating plastic resin layer 388 and mold cavities in the forming mold to create hooks 390 or hook performs on plastic resin layer 388. The stretchy quality of non-woven material 382 allows a wearer to stretch diaper tab 380 to form a good fit by releasably engaging hooks 390 with the diaper chassis.

In another variation of material 102 illustrated in FIG. 1A, referring to FIG. 8, composite material 400 is formed using the calender stack 100 configured to join materials 402 and 404 with plastic lane 406 having a folding element 408 (e.g., V shaped notch 408). Plastic lane 406 bridges a gap 410 between 402 and 404. Plastic lane 406 is sufficiently deformable such that material 404 can be folded over to touch material 402. Additional plastic hook lanes 412 and 414 are created by mold cavities in the mold roll. Continuous composite material 400 can be at a selected repeat length to form individual double closure fasteners for diapers.

Referring to FIG. 8A, diaper 430 includes diaper chassis 432 and diaper flap 434. Double closure fastener 436 is bonded to diaper chassis 432. Double closure fastener 436 uses two sets of hook rows to releasably attach to non-woven loop material of diaper chassis 432. Accordingly, double closure fastener 436 releasably attaches diaper flap 434 to diaper chassis 432.

One example of double closure fastener 436, referring to FIG. 8B, is double closure fastener 450. Double closure fastener 450 includes material 452 joined to folded material 454 using plastic lane 406 having a folding element (e.g., V shaped notch). Plastic lane 406 is sufficiently deformable such that material 454 can be folded over to touch material 452 by compressing the folding element (e.g., V shaped notch). Material 452 and one side of folded material 454 are ultrasonically bonded to diaper chassis 432. In one variation of this example, materials 452 and 454 are preformed spunbond material. A continuous material for double closure fastener 450 is manufactured by feeding material 452 and folded material 454 into a configuration of the calender stack. Plastic resin from the extruder laminates plastic lane 406 and hook lanes 412 and 414 onto materials 452 and 454. This continuous material is cut at a running length to form individual double closure fasteners 450. Referring to FIG. 8C, double closure fastener 450 is used to releasably engage diaper flap 434 by releasably engaging hook lanes 412 with loops on one side of diaper flap 434 and releasably engaging hook lanes 414 with loops on the other side of diaper flap 434.

Figure 8D:
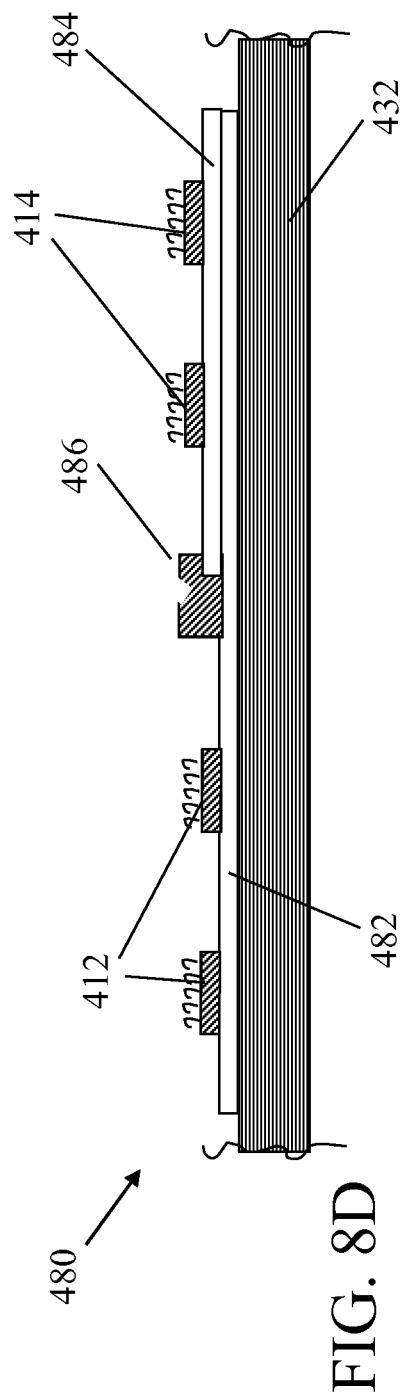
FIG. 8D is a view of another double closure fastener of FIG. 8A in an open position.
Figure 8E:
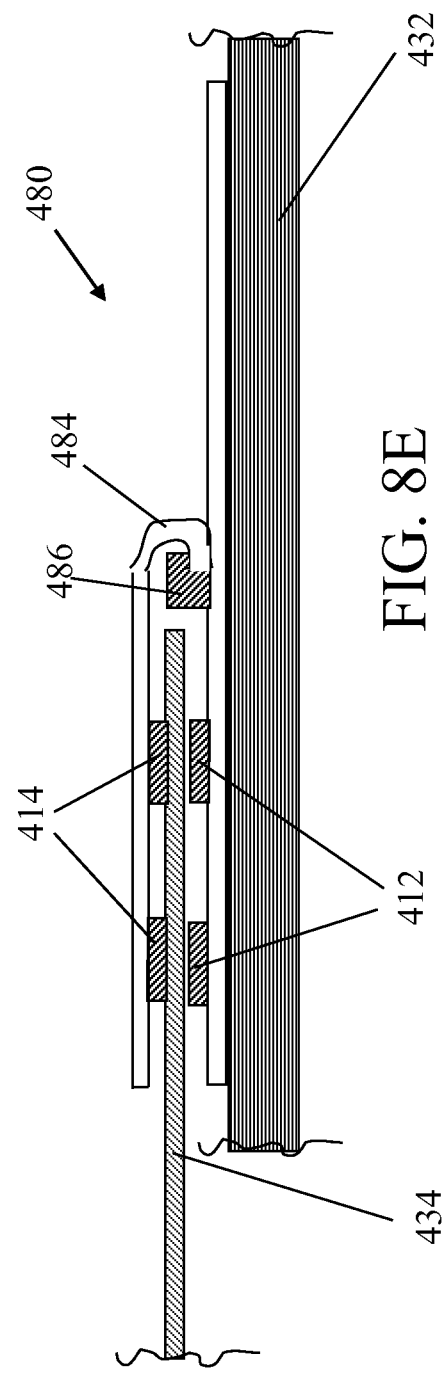
FIG. 8E is a view of the double closure fastener of FIG. 8D in a closed position releasably attached to a diaper flap.

Another example of double closure fastener 436, referring to FIG. 8D, is double closure fastener 480. Double closure fastener 480 includes a length of material 482 and a shorter length of material 484 laid on top of the length of material 482. Materials 482 and 484 are joined by a plastic lane 486 with a folding element (e.g., V shaped notch). Plastic lane 486 joins materials 482 and 484 at the exterior interface of the overlap of materials 482 and 484 similar to plastic lane 256 illustrated in FIG. 4. Plastic lane 486 is sufficiently deformable such that material 484 can be folded over to touch material 482 by compressing the folding element (e.g., V shaped notch) between materials 484 and 482. The length of material 482 is ultrasonically bonded to diaper chassis 432. In one variation of this example, materials 482 and 484 are made of preformed spunbond material. Plastic hook lanes 412 and 414 are laminated onto materials 482 and 484, respectively. A continuous material for double closure fastener 480 is manufactured by feeding material 484 on top of material 482 into a configuration of the calender stack. Plastic resin from the extruder laminates plastic lane 486 and hook lanes 412 and 414 onto materials 482 and 484. This continuous material is cut at a running length to form individual double closure fasteners 450. Referring to FIG. 8E, double closure fastener 480 is used to releasably engage diaper flap 434 by releasably engaging hook lanes 412 with loops on one side of diaper flap 434 and releasably engaging hook lanes 414 with loops on the other side of diaper flap 434.

Figure 9A:
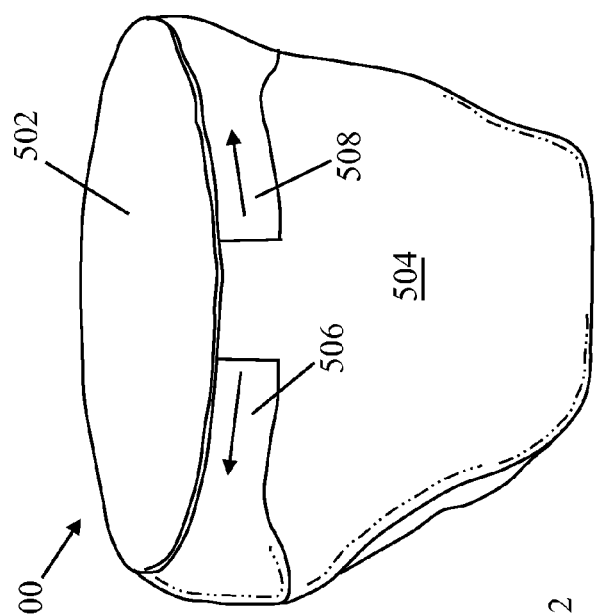
FIG. 9A is a view of the absorbant articles of FIG. 9 that are loosened by tearing the tear fastener.
Figure 9B:
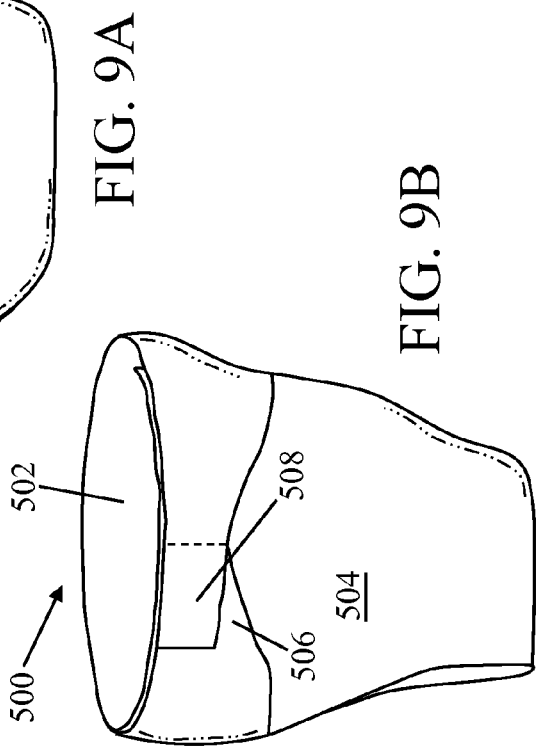
FIG. 9B is a view of the absorbant articles of FIG. 9A that are tightened after tearing the tear fastener.
Figure 9:
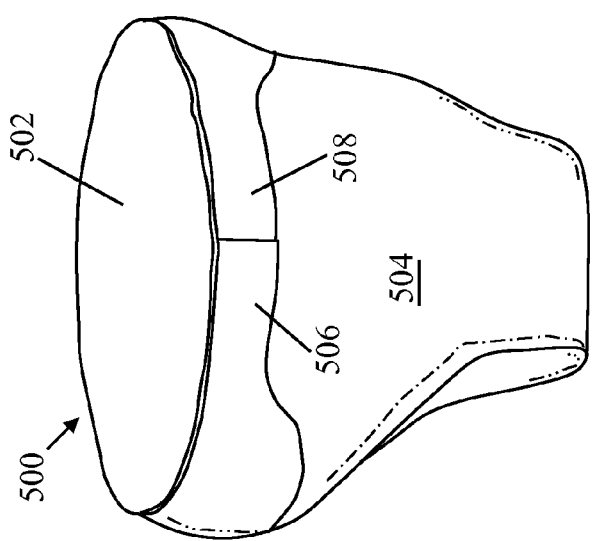
FIG. 9 is a view of a pair of absorbant articles with a tear fastener.

Referring to FIG. 9, absorbant articles 500 include an opening 502 for a wearer to step into, and a chassis 504. Absorbant articles 500 can be disposable sanitary pants or any similar disposable article that is worn and absorbent. Absorbant articles 500 also include a pair of flaps 506 and 508. Flaps 506 and 508 are sealed together using a composite material formed using a configuration of the above described calender stack. This composite material has a plastic lane with hooks that releasably engage with loops on chassis 504. The plastic lane can be ripped into two plastic lanes with hooks to take off the soiled absorbant articles 500 without sliding the articles down the legs of a wearer. Referring to FIG. 9A, these two plastic lanes can also be reattached to chassis 504 to increase the opening 502 for the wearer. Referring to FIG. 9B, these two plastic lanes can be reattached so that flap 508 attaches onto flap 506 to decrease the opening 502 for the wearer. Increasing or decreasing the opening 502 creates flexibility for the usage of the absorbant articles 500. Furthermore, the two plastic lanes can be reattached for repositioning, if for example, there is a need to look inside the absorbant articles 500. In this case, the opening 502 is not increased or decreased after reattachment.

Referring to FIG. 10, the pair of flaps 506 and 508 are detachably attached to chassis 504 using a strip of composite material 512 that is attached to flaps 506 and 508. The strip of composite material 512 can be attached to the flaps 506 and 508 using ultrasonic welding, glue, or other means of adhesion. Composite material 512 includes a material 530 and a material 532 joined by plastic lane 534 with hooks. In one variation, materials 530 and 532 are formed of spunbond material. Composite material 512 is manufactured using a configuration of the calender stack as illustrated in FIG. 1. Materials 530 and 532 are fed into the calender stack and the extruder extrudes a sheet of plastic resin to form plastic lane 534. Mold cavities in the mold roll form hooks or hook performs in plastic lane 534. In the interface between materials 530 and 532 there is a gap 536. Flaps 506 and 508 can form a butt joint at gap 536. The resin for plastic lane 534 is chosen so that plastic lane 534 can be ripped. In some examples, a notch or other splittable feature can be formed in the middle of plastic lane 534 to facilitate ripping plastic lane 534 along gap 536. Composite material 512 is cut into individual pieces that are ultrasonically welded to flaps 506 and 508.

In a variation of the composite material of FIG. 10, plastic hook lane 534 is a lane of discontinuous hook islands (132', 132") as shown in FIG. 1D. This can increase the flexibility of gap 536 to increase the opening 502 as illustrated in FIG. 1E.

Figure 10D:
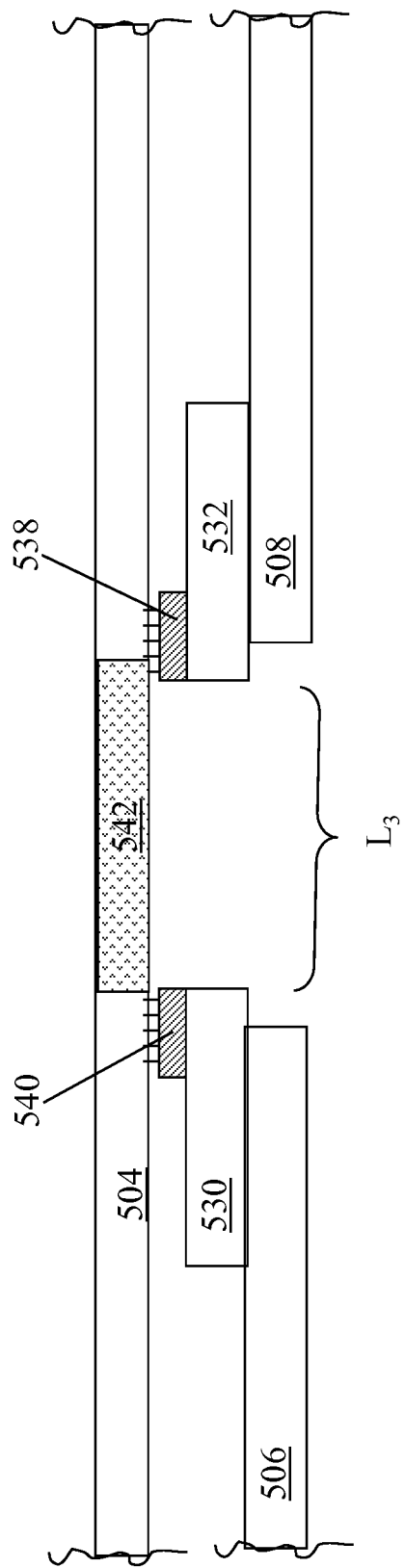
FIG. 10D is a view of the tear fastener of FIG. 10 that allows stretch of the absorbant articles.

After ripping plastic lane 534, as shown in FIG. 10A, gap 537 exists in the middle of plastic lane 534 creating plastic lanes 538 and 540. FIG. 10B shows how the opening 502 of the absorbant articles 500 can be enlarged by a distance $L_1$ by reattaching plastic hook lanes 538 and 540 to chassis 504. FIG. 10C shows how opening 502 of absorbant articles 500 is decreased by a distance L2 by attaching plastic hook lane 538 to loops of flap 506 while leaving plastic hook lane 540 releasably engaged with loops of chassis 504. In addition to enlarging or decreasing opening 502, the fit of the absorbant articles 500 can also be modified by attaching plastic hook lane 538 to other sections of chassis 504. FIG. 10D shows how ripping plastic lane 534 allows the absorbant articles 500 to handle stretch in region 542 of the chassis 504 by leaving the separate plastic hook lanes engaged with loops of chassis 504.

A number of embodiments of the invention have been described. Nevertheless, it will be understood that various modifications may be made without departing from the spirit and scope of the invention. Accordingly, other embodiments are within the scope of the following claims.

What is claimed is:

1. A disposable absorbent article comprising:
   a chassis having a first end and a second end that are opposite to one another;
   an engageable material attached to the chassis adjacent to the two ends; and
   a double closure system attached to the chassis adjacent to one of the two ends opposite the end to which the engageable material is attached, the double closure system comprising a first lane of plastic resin extending across an interface of first and second materials, wherein the first lane of plastic resin is bonded to the first and second materials such that the first and second materials are permanently joined by the first lane of resin;
   wherein the double closure system or the engageable material comprises an array of fastener elements extending from one side of a second lane of plastic resin, the fastener elements comprising engageable heads on stems integrally formed with the second lane of the plastic resin; and
   wherein the double closure system releasably engages the engageable material to secure the disposable absorbent article to a wearer.

2. The disposable absorbent article of claim 1 wherein the engageable material has hook engageable loops.

3. The disposable absorbent article of claim 1 wherein the first and second ends form a butt joint.

4. The disposable absorbent article of claim 1 wherein the engageable material is located on two opposite sides of the double closure system.

5. The disposable absorbent article of claim 1 wherein the first lane of plastic resin has a folding feature comprising a V-shaped notch.

6. The disposable absorbent article of claim 5 wherein the first lane of plastic resin is spaced apart from a second lane of plastic resin, the second lane of plastic resin having an array of fastener elements comprising engageable heads on stems integrally formed with the second lane of the plastic resin.

7. The disposable absorbent article of claim 6 wherein the second lane of plastic resin is located on the first material.

8. The disposable absorbent article of claim 6 wherein the second lane of plastic resin is located on the second material.

9. The disposable absorbent article of claim 8 further comprising, on the first material, a third lane of the plastic resin with which the fastener elements are integrally formed.

10. The disposable absorbent article of claim 9 wherein the second material is pivotable about the folding feature to releasably engage the engageable material.

11. The disposable absorbent article of claim 10 wherein the first lane of resin is bonded to a first end of the second material.

12. The disposable absorbent article of claim 10 wherein the first lane of resin is bonded to a middle portion of the second material.

* * * * *